United States Patent
Sun et al.

(10) Patent No.: US 11,071,857 B2
(45) Date of Patent: Jul. 27, 2021

(54) SYSTEMS AND METHODS FOR WIRELESS TREATMENT OF ARRHYTHMIAS

(71) Applicants: WILLIAM MARSH RICE UNIVERSITY, Houston, TX (US); TEXAS HEART INSTITUTE, Houston, TX (US); BAYLOR COLLEGE OF MEDICINE, Houston, TX (US)

(72) Inventors: Yuxiang Sun, Houston, TX (US); Aydin Babakhani, Houston, TX (US); Mehdi Razavi, Houston, TX (US); David Burkland, Houston, TX (US); Brian Greet, Houston, TX (US); Mathews John, Houston, TX (US); Hongming Lyu, Houston, TX (US)

(73) Assignees: William Marsh Rice University, Houston, TX (US); Baylor College of Medicine, Houston, TX (US); Texas Heart Institute, Houston, TX (US)

( * ) Notice: Subject to any disclaimer, the term of this patent is extended or adjusted under 35 U.S.C. 154(b) by 0 days.

(21) Appl. No.: 16/327,230

(22) PCT Filed: Aug. 22, 2017

(86) PCT No.: PCT/US2017/047901
§ 371 (c)(1),
(2) Date: Feb. 21, 2019

(87) PCT Pub. No.: WO2018/039162
PCT Pub. Date: Mar. 1, 2018

(65) Prior Publication Data
US 2019/0224476 A1    Jul. 25, 2019

Related U.S. Application Data

(60) Provisional application No. 62/518,220, filed on Jun. 12, 2017, provisional application No. 62/378,012, filed on Aug. 22, 2016.

(51) Int. Cl.
*A61N 1/02* (2006.01)
*A61N 1/05* (2006.01)
(Continued)

(52) U.S. Cl.
CPC .......... *A61N 1/0563* (2013.01); *A61N 1/025* (2013.01); *A61N 1/059* (2013.01); *A61N 1/0573* (2013.01);
(Continued)

(58) Field of Classification Search
CPC .............. A61N 1/0563; A61N 1/37217; A61N 1/37223; A61N 1/3975; A61N 1/025;
(Continued)

(56) References Cited

U.S. PATENT DOCUMENTS

| | | |
|---|---|---|
| 4,388,927 A | 6/1983 | Schober |
| 4,612,940 A | 9/1986 | Kasevich et al. |

(Continued)

FOREIGN PATENT DOCUMENTS

| | | |
|---|---|---|
| CN | 104767291 A | 7/2015 |
| WO | 2007/109656 A2 | 9/2007 |

(Continued)

OTHER PUBLICATIONS

International Search Report and Written Opinion dated Mar. 14, 2018 for International application PCT/US2017/0047901 filed Aug. 22, 2017, 17 pages.
(Continued)

*Primary Examiner* — Carl H Layno
*Assistant Examiner* — Anh-Khoa N Dinh
(74) *Attorney, Agent, or Firm* — Dickinson Wright PLLC; Ross Spencer Garsson; Mark E. Scott

(57) ABSTRACT

Wireless treatment of arrhythmias. At least some of the example embodiments are methods including: charging a capacitor of a first microchip device abutting heart tissue, the
(Continued)

charging by harvesting ambient energy; charging a capacitor of a second microchip device abutting the heart tissue, the charging of the capacitor of the second microchip device by harvesting ambient energy; sending a command wirelessly from a communication device outside the rib cage to the microchip devices; applying electrical energy to the heart tissue by the first microchip device responsive to the command, the electrical energy applied from the capacitor of the first microchip device; and applying electrical energy to the heart tissue by the second microchip device responsive to the command to the second microchip device, the electrical energy applied from the capacitor of the second microchip device.

40 Claims, 10 Drawing Sheets

(51) Int. Cl.
    *A61N 1/372*     (2006.01)
    *A61N 1/375*     (2006.01)
    *A61N 1/378*     (2006.01)
    *A61N 1/39*     (2006.01)

(52) U.S. Cl.
    CPC ....... *A61N 1/3787* (2013.01); *A61N 1/37217* (2013.01); *A61N 1/37223* (2013.01); *A61N 1/37229* (2013.01); *A61N 1/37288* (2013.01); *A61N 1/37516* (2017.08); *A61N 1/37518* (2017.08); *A61N 1/3968* (2013.01); *A61N 1/3975* (2013.01); *A61N 1/39622* (2017.08)

(58) Field of Classification Search
    CPC .... A61N 1/0573; A61N 1/059; A61N 1/3968; A61N 1/37288; A61N 1/37516; A61N 1/3787; H04L 49/109
    USPC ...................................................... 607/116
    See application file for complete search history.

(56) References Cited

U.S. PATENT DOCUMENTS

| | | | |
|---|---|---|---|
| 4,719,919 A | | 1/1988 | Marchosky et al. |
| 5,464,429 A | | 11/1995 | Hedberg et al. |
| 5,749,909 A | | 5/1998 | Schroeppel et al. |
| 7,043,301 B1 | | 5/2006 | Kroll et al. |
| 8,634,919 B1 * | | 1/2014 | Hou ..................... A61N 1/368 607/36 |
| 9,037,223 B2 | | 5/2015 | Oral et al. |
| 2002/0103507 A1 * | | 8/2002 | Helland ............... A61N 1/3918 607/5 |
| 2003/0032986 A1 | | 2/2003 | Kupper |
| 2004/0095287 A1 | | 5/2004 | Mohamadi |
| 2007/0293895 A1 | | 12/2007 | Cowan et al. |
| 2008/0021505 A1 | | 1/2008 | Hastings et al. |
| 2008/0262580 A1 | | 10/2008 | Gerber et al. |
| 2008/0300660 A1 * | | 12/2008 | John ..................... H02J 50/50 607/61 |
| 2010/0076517 A1 * | | 3/2010 | Imran .................. A61N 1/3629 607/35 |
| 2013/0123882 A1 | | 5/2013 | Towe |
| 2014/0046389 A1 | | 2/2014 | Anderson et al. |
| 2014/0243848 A1 * | | 8/2014 | Auricchio .......... A61N 1/37205 606/129 |
| 2015/0127068 A1 * | | 5/2015 | Simon ................ A61N 1/36153 607/60 |
| 2015/0217123 A1 | | 8/2015 | Deterre et al. |
| 2015/0343205 A1 | | 12/2015 | Howard et al. |
| 2018/0235692 A1 | | 8/2018 | Efimov et al. |

FOREIGN PATENT DOCUMENTS

| | | |
|---|---|---|
| WO | 2018/053467 A1 | 3/2018 |
| WO | 2018039162 A2 | 3/2018 |

OTHER PUBLICATIONS

International Search Report and Written Opinion dated Dec. 12, 2017 for International application PCT/US2017/052163 filed Sep. 19, 2017, 17 pages.

Derksen M.D., Richard et al., "Tissue Discontinuities Affect Conduction Velocity Restitution, A Mechanism by Which Structural Barriers May Promote Wave Break," http://circ.ahajournals.org/content/108/7/882, Aug. 19, 2003, 8 pages, Copyright 2003 American Heart Association, Inc.

Fenton PhD, Flavio H. et al., "Termination of Atrial Fibrillation Using Pulsed Low-Energy Far-Field Stimulation," http://circ.ahajournals.org/content/120/6/467, Aug. 11, 2009, 15 pages, Copyright 2009 American Heart Association, Inc.

Sun, Yuxiang et al., "A Wirelessly Powered Injection-Locked Oscillator with On-Chip Antennas in 180nm SOI CMOS," IEEE Paper 978-1-5090-0698-4/16, 3 pages, Copyright 2016 IEEE.

Ramrakhyani, Anil Kumar et al., "Design and Optimization of Resonance-Based Efficient Wireless Power Delivery Systems for Biomedical Implants," IEEE Transactions on Biomedical Circuits and Systems, vol. 5, No. 1, Feb. 2011, 16 pages, Copyright 2010 IEEE.

Li, Xing et al., "A 13.56 MHz Wireless Power Transfer System With Reconfigurable Resonant Regulating Rectifier and Wireless Power Control for Implantable Medical Devices," IEEE Journal of Solid-State Circuits, vol. 50, No. 4, Apr. 2015,12 pages, Copyright 2015 IEEE.

Ho, John S. et al., "Wireless power transfer to deep-tissue microimplants," PNAS, Jun. 3, 2014, vol. 11, No. 22, www.pnas.org/cgi/content/short/1403002111, 12 pages.

Lepock, James R., "Cellular effects of hyperthermia: relevance to the minimum dose for thermal damage," International Journal of Hyperthermia, vol. 19:3, pp. 252-266, 2003, Copyright 2003 Taylor & Francis Ltd.

International Searching Authority, International Search Report and Written Opinion for International Application No. PCT/US2020/049349, dated Nov. 24, 2020; 8 pages.

International Searching Authority, International Search Report and Written Opinion for International Application No. PCT/US2019/062443, dated Jan. 29, 2020; 8 pages.

H. Lyu et al., "A Multi-site Heart Pacing Study Using Wirelessly Powered Leadless Pacemakers," 2018 40th Annual International Conference of the IEEE Engineering in Medicine and Biology Society (EMBC), Honolulu, HI, 2018, pp. 3434-3437, doi: 10.1109/EMBC.2018.8512977.; Retrieved from Internet on Nov. 16, 2020; <https://ieeexplore.ieee.org/abstract/document/8512977>; entire document.

International Searching Authority, International Search Report and Written Opinion for International Application No. PCT/US21/21467, dated Jun. 3, 2021; 9 pages.

\* cited by examiner

SYSTEMS AND METHODS FOR WIRELESS TREATMENT OF ARRHYTHMIAS

CROSS-REFERENCE TO RELATED APPLICATIONS

This application is a U.S. National Phase Entry of PCT application serial no. PCT/US2017/047901 filed Aug. 22, 2017 and titled "Systems and Methods for Wireless Treatment of Arrhythmias." The PCT application claims priority to U.S. Patent Application Ser. No. 62/378,012 filed Aug. 22, 2016 titled "Systems And Methods For Wireless Defibrillation," and U.S. Patent Application Ser. No. 62/518,220 filed Jun. 12, 2017 titled "Systems And Methods For Wireless Defibrillation." The PCT application and the provisional applications are hereby incorporated by reference in their entirety for all purposes.

TECHNICAL FIELD

Various embodiments are directed to systems and methods for pacing and defibrillation of heart tissue. More particularly, various embodiments are directed to wireless pacing and defibrillation utilizing a wireless microchip device array.

BACKGROUND

There are over three million people worldwide who have a pacemaker implanted. Pacemakers are used to treat a variety of cardiac conditions, such as atrioventricular block and symptomatic bradycardia. Pacemakers are used to manage hearts that have aberrant intrinsic pacing. Additionally, pacemakers have demonstrated the ability to improve cardiac function and quality of life in patients with reduced left ventricular systolic function and significant conduction system disease by way of coordinated pacing of both the left and the right ventricle.

Related-art pacemakers consist of two primary components: 1) a generator, containing the electrical components and a battery; and 2) leads which transmit the electrical signals from an electrical enclosure (sometimes referred to as a "can") to the heart tissue, and such leads can be positioned in the right atrium, right ventricle, and the left ventricle by way of the coronary venous system. There have been a number of issues related to leads that can cause significant complications in patients, including the development of scar tissue of the lead resulting in complete blood vessel occlusion and an increased risk of infection. Additionally, given the non-rechargeable nature of the related-art pacemakers, there is substantial risk for complication with each subsequent replacement of the battery, including a significant risk for infection.

SUMMARY

The present invention regards systems and methods for pacing and defibrillation of heart tissue. More particularly, various embodiments are directed to wireless pacing and defibrillation utilizing a wireless microchip device array.

In general, in one aspect, the invention features an implantable medical device for applying electrical energy to heart tissue. The implantable medical device includes a substrate of semiconductor material. The implantable medical device further includes an anchoring structure mechanically coupled to the substrate. The implantable medical device further includes a capacitor associated with the substrate. The implantable medical device further includes an energy harvesting circuit defined on the substrate and electrically coupled to the capacitor, the energy harvesting circuit configured to extract electrical energy from energy propagating proximate the device and to store electrical energy on the capacitor. The implantable medical device further includes a communication circuit defined on the substrate, the communication circuit electrically coupled to the energy harvesting circuit, the communication circuit configured to receive commands originated external to the implantable medical device. The implantable medical device further includes an energy delivery circuit defined on the substrate, the energy delivery circuit electrically coupled to a set of electrodes, electrically coupled to the energy harvesting circuit, and communicatively coupled to the communication circuit. The energy delivery circuit configured to provide electrical energy to the heart tissue across the set of electrodes responsive to the commands received by the communication circuit.

Implementations of the invention can include one or more of the following features:

The communication circuit further includes a communication antenna defined on the substrate, the communication antenna can operate at a frequency above 1 Mega Hertz (MHz). The communication circuit can be configured to receive commands from an external device by way of the communication antenna.

The energy harvesting circuit can further include an energy harvesting antenna defined on the substrate, the energy harvesting antenna has an operating frequency above 1 Mega Hertz (MHz). The energy harvesting circuit can further include a rectifier defined on the substrate, the rectifier electrically coupled between the energy harvesting antenna and the capacitor, the rectifier configured to rectify alternating current energy from the energy harvesting antenna to create rectified energy stored on the capacitor. The energy harvesting circuit can further include a power management unit defined on the substrate, the power management unit coupled to the capacitor, the power management unit configured to produce a regulated direct current (DC) voltage from rectified energy stored on the capacitor.

The energy harvesting circuit can further include a set of conductive pads. The energy harvesting circuit can further include a rectifier defined on the substrate, the rectifier electrically coupled between the second set of conductive pads and the capacitor, the rectifier circuit configured to rectify alternating current energy flowing through the second set of conductive pads to create rectified energy stored on the capacitor. The energy harvesting circuit can further include a power management unit defined on the substrate, the power management unit coupled to the capacitor, the power management unit configured to produce a regulated DC voltage from the rectified energy stored on the capacitor.

The capacitor can be at least one selected from a group that includes a capacitor defined on the substrate; a capacitor mechanically coupled to the substrate; and a capacitor mechanically coupled to the anchoring structure.

The implantable medical device can further include a sensing circuit defined on the substrate, the sensing circuit electrically coupled to the energy harvesting circuit and communicatively coupled to the communication circuit. The sensing circuit can be configured to sense electrical impulses propagating through heart tissue, and configured to trigger the communication circuit to send a message responsive to the electrical impulses propagating through the heart tissue.

The sensing circuit can further include a set of conductive pads. The sensing circuit can be configured to sense electrical impulses propagating through heart tissue by detecting at least one selected from a group that includes: electrical current flow through the set of conductive pads; and voltage across the set of conductive pads.

The sensing circuit can further include a loop antenna defined on the substrate, the sensing circuit electrically coupled to the loop antenna. The sensing circuit can be configured to sense electrical impulses propagating through heart tissue based on electrical current induced in the loop antenna.

The implantable medical device can further include a means for mechanically coupling anchoring structure to the heart tissue.

The implantable medical device can further include a structure to mechanically couple the anchoring structure to heart tissue that includes at least one selected from a group that includes: a helical screw mechanically coupled to the anchoring structure opposite the substrate; a pin that defines a distal end with a barb defined thereon, the pin mechanically coupled to the anchoring structure; and a plurality of pins that each define a distal end with a barb thereon, the pins mechanically coupled to the anchoring structure; a helical screw mechanically coupled to the anchoring structure opposite the substrate and electrically coupled to an electrode of the set of electrodes; a pin that defines a distal end with a barb defined thereon, the pin mechanically coupled to the anchoring structure and electrically coupled to an electrode of the set of electrodes; and a plurality of pins that each define a distal end with a barb thereon, the pins mechanically coupled to the anchoring structure, and each pin electrically coupled to a respective electrode of the set of electrodes.

In general, in another aspect, the invention features a sensing device for detecting electrical impulses propagating through heart tissue. The sensing device includes a substrate of semiconductor material. The sensing device further includes an anchoring structure mechanically coupled to the substrate. The sensing device further includes a capacitor associated with the substrate. The sensing device further includes an energy harvesting circuit defined on the substrate and electrically coupled to the capacitor, the energy harvesting circuit configured to extract electrical energy from energy propagating proximate the sensing device and to store electrical energy on the capacitor. The sensing device further includes a communication circuit defined on the substrate, the communication circuit electrically coupled to the energy harvesting circuit, the communication circuit configured to receive commands originated external to the sensing device. The sensing device further includes a sensing circuit defined on the substrate, the sensing circuit electrically coupled to the energy harvesting circuit and communicatively coupled to the communication circuit. The sensing circuit configured to sense electrical impulses propagating through the heart tissue, and configured to trigger the communication circuit to send a message responsive to the electrical impulses propagating through the heart tissue.

Implementations of the invention can include one or more of the following features:

The sensing circuit can further include a set of sensing conductive pads, the sensing circuit electrically coupled to the set of sensing conductive pads. The sensing circuit can be configured to sense the electrical impulses propagating through heart tissue by detecting at least one selected from a group that includes: electrical current flow through the set of sensing electrodes; and voltage across the set of sensing conductive pads.

The sensing circuit can further include a loop antenna defined on the substrate, the sensing circuit electrically coupled to the loop antenna. The sensing circuit can be configured to sense the electrical impulses propagating through heart tissue based on electrical current induced in the loop antenna.

The energy harvesting circuit can further include an energy harvesting antenna defined on the substrate, the energy harvesting antenna has an operating frequency above 1 Mega Hertz (MHz). The energy harvesting circuit can further include a rectifier defined on the substrate, the rectifier electrically coupled between the energy harvesting antenna and the capacitor, the rectifier configured to rectify alternating current energy from the energy harvesting antenna to create rectified energy stored on the capacitor. The energy harvesting circuit can further include a power management unit defined on the substrate, the power management unit coupled to the capacitor, the power management unit configured to produce a regulated DC voltage from the rectified energy stored on the capacitor.

The energy harvesting circuit can further include a set of conductive pads. The energy harvesting circuit can further include a rectifier defined on the substrate, the rectifier electrically coupled between the second set of conductive pads and the capacitor, the rectifier configured to rectify alternating current energy flowing through the second set of conductive pads to create rectified energy stored on the capacitor. The energy harvesting circuit can further include a power management unit defined on the substrate, the power management unit coupled to the capacitor, the power management unit configured to produce a regulated DC voltage from rectified energy stored on the capacitor.

The capacitor can be at least one selected from a group that includes the capacitor is defined on the substrate; the capacitor is mechanically coupled to the substrate; and the capacitor is mechanically coupled to the anchoring structure.

The sensing device can further include a means for mechanically coupling the anchoring structure to the heart tissue.

The sensing device can further include a structure to mechanically couple the anchoring structure to the heart tissue including at least one selected from a group that includes: a helical screw mechanically coupled to the anchoring structure opposite the substrate; a pin that defines a distal end with a barb defined thereon, the pin mechanically coupled to the anchoring structure; and a plurality of pins that each define a distal end with a barb thereon, the pins mechanically coupled to the anchoring structure.

In general, in another aspect, the invention features a system for treating arrhythmias in heart tissue. The system includes a plurality of microchip devices without batteries. Each microchip device includes a substrate of semiconductor material. Each microchip device further includes a capacitor associated with the substrate. Each microchip device further includes an energy harvesting circuit defined on the substrate and electrically coupled to the capacitor, the energy harvesting circuit configured to extract electrical energy from energy propagating proximate the microchip device and to store electrical energy on the capacitor. Each microchip device further includes a communication circuit defined on the substrate, the communication circuit electrically coupled to the energy harvesting circuit, the communication circuit configured to receive commands originated external to the microchip device. Each microchip device further includes an energy delivery circuit defined on the substrate, the energy delivery circuit electrically coupled to a set of electrodes, electrically coupled to the energy harvesting circuit, and communicatively coupled to the communication circuit. The energy delivery circuit configured to provide electrical energy to heart tissue across the set of electrodes responsive to the commands received by the communication circuit. The system further includes each microchip device mechanically coupled to the heart tissue, and the set of electrodes of each microchip device electrically coupled to the heart tissue. The system further includes a communication device distinct from the plurality of microchip devices, the communication device communicatively coupled to the communication device of each of the plurality of microchip devices. The plurality of microchip devices configured to apply electrical energy to the heart tissue responsive to commands from the communication device.

Implementations of the invention can include one or more of the following features:

The communication device can be configured to defibrillate the heart tissue by a command to the plurality of microchip devices to substantially simultaneously apply electrical energy.

The communication device can be configured to pace the heart tissue by a command to the plurality of microchip devices to apply electrical energy sequentially along a predefined path, the predefined path intersects the plurality of microchip devices.

The communication device can be at least one selected from the group that includes: subcutaneously disposed; and external to a body containing the heart.

The communication device can include an antenna, and the communication device is configured to transmit electromagnetic waves toward the microchip devices. The energy harvesting circuit of the microchip device can be configured to extract the energy from the electromagnetic waves transmitted by the communication device.

The energy harvesting circuit of the microchip device can be configured to harvest energy from electrical impulses in the heart tissue.

The communication device can include a set of conductive pads electrically coupled to the body, and the communication device is configured to induce electrical current flow proximate to the plurality of microchip devices. The energy harvesting circuit of the microchip device can be configured to extract the energy from the electrical current flow.

In general, in another aspect, the invention features a method of treating arrhythmias in heart tissue. The method includes charging a capacitor of a first microchip device abutting the heart tissue, the charging by harvesting ambient energy by the first microchip device. The method further includes charging a capacitor of a second microchip device abutting the heart tissue, the charging of the capacitor of the second microchip device by harvesting ambient energy by the second microchip device, and the second microchip spaced apart from the first microchip device. The method further includes sending a command wirelessly from a communication device outside the rib cage to the first microchip device. The method further includes sending a command wirelessly from the communication device to the second microchip device. The method further includes applying electrical energy to the heart tissue by the first microchip device responsive to the command to the first microchip device, the electrical energy applied from the capacitor of the first microchip device. The method further includes applying electrical energy to the heart tissue by the second microchip device responsive to the command to the second microchip device, the electrical energy applied from the capacitor of the second microchip device.

Implementations of the invention can include one or more of the following features:

The method can further include defibrillating the heart tissue by simultaneously applying electrical energy by the first microchip device and the second microchip device.

The method can further include pacing the heart tissue by sequentially applying electrical energy by the first microchip device and the second microchip device.

The method can further include sensing electrical impulses sourced by and propagating through the heart tissue, the sensing by the first microchip device. The method can further include sending an indication of the electrical signal from the first microchip device to the communication device, the sending wirelessly. The method can further include sending the commands by the communication device responsive to the indication of the electrical impulse from the first microchip device.

The method can further include charging a capacitor of a third microchip device, the third microchip device distinct from the first and second microchip devices, the third microchip device abutting the heart tissue at a spaced apart location from the first and second microchip devices, and the charging by harvesting ambient energy by the third microchip device. The method can further include sensing electrical impulses sourced by and propagating through the heart tissue, the sensing by the third microchip device. The method can further include sending an indication of the electrical impulse from the third microchip device to the communication device, the sending wirelessly. The method can further include sending the commands by the communication device responsive to the indication of the electrical signal from the third microchip device.

Charging the first capacitor can further include harvesting electrical energy from electromagnetic waves sourced by the communication device.

Charging the first capacitor can further include harvesting electrical energy from electrical current sourced by the communication device.

Charging the first capacitor can further include harvesting electrical energy from electrical impulses sourced by and propagating through the heart tissue.

In general, in another aspect, the invention features a system of microchip devices for implantation abutting heart tissue. The system includes a carrier structure that defines a length. The system further includes a plurality of microchip devices mechanically coupled to the carrier structure at spaced apart locations along the carrier structure. Each microchip device further includes a substrate of semiconductor material. Each microchip device further includes a capacitor associated with the substrate. Each microchip device further includes an energy harvesting circuit defined on the substrate and electrically coupled to the capacitor, the energy harvesting circuit configured to extract electrical energy from energy propagating proximate the microchip device and to store electrical energy on the capacitor. Each microchip device further includes a communication circuit defined on the substrate, the communication circuit electrically coupled to the energy harvesting circuit, the communication circuit configured to receive commands originated external to the microchip device. Each microchip device further includes an energy delivery circuit defined on the substrate, the energy delivery circuit electrically coupled to a set of electrodes, electrically coupled to the energy harvesting circuit, and communicatively coupled to the communication circuit. The energy delivery circuit configured to provide electrical energy to heart tissue across the set of electrodes responsive to the commands received by the communication circuit.

Implementations of the invention can include one or more of the following features:

The carrier structure can be a metallic wire and the plurality of microchip devices are mechanically coupled to the metallic wire at spaced apart locations along a longitudinal axis of the wire.

The carrier structure can be a stent of metallic material, and the plurality of microchip devices are mechanically coupled to the stent at spaced apart locations along a longitudinal axis of the stent.

The plurality of microchip devices can be also spaced around the stent at distinct radial locations relative to the longitudinal axis of the stent.

The carrier structure can be a metal wire that defines a helix, and wherein the plurality of microchip devices are mechanically coupled to the metallic wire at spaced apart locations along the helix.

BRIEF DESCRIPTION OF THE DRAWINGS

For a detailed description of example embodiments, reference will now be made to the accompanying drawings (not necessarily to scale) in which.

DEFINITIONS

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Abutting [ ] heart tissue" shall mean that a device is mechanically coupled to heart tissue such that the device moves with the heart during contract and relaxation of the heart tissue. The "[ ]" refers to the presence or absence of articles (e.g., "a" and "the"), and the presence or absence of articles shall not obviate applicability of the definition.

"Electromagnetic waves" shall mean alternating electric and magnetic fields propagating through a medium.

"Substantially simultaneously" in the context of a plurality microchip devices applying electrical energy shall mean the plurality of microchip devices starting the application of energy to the heart tissue within 200 microseconds of each other.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various embodiments are directed to systems and related methods to defibrillate or pace the heart when there is an arrhythmic event. This system may include a network of treatment devices (referred to herein as "microchip devices") which may provide defibrillating and/or pacing. The microchip devices do not have batteries and are capable of applying electrical energy to the heart tissue. In some cases, microchip devices sense electrical impulses sourced by the heart, and send indications of the electrical impulses to a communication device that controls the array of microchip devices. The communication device may be wirelessly and communicatively coupled to the microchip devices to receive indications of electrical impulses in the heart, and to control application and timing of electrical energy for defibrillation and pacing. The description starts with a high level overview of the system, and then describes the various components in greater detail.

Figure 1:
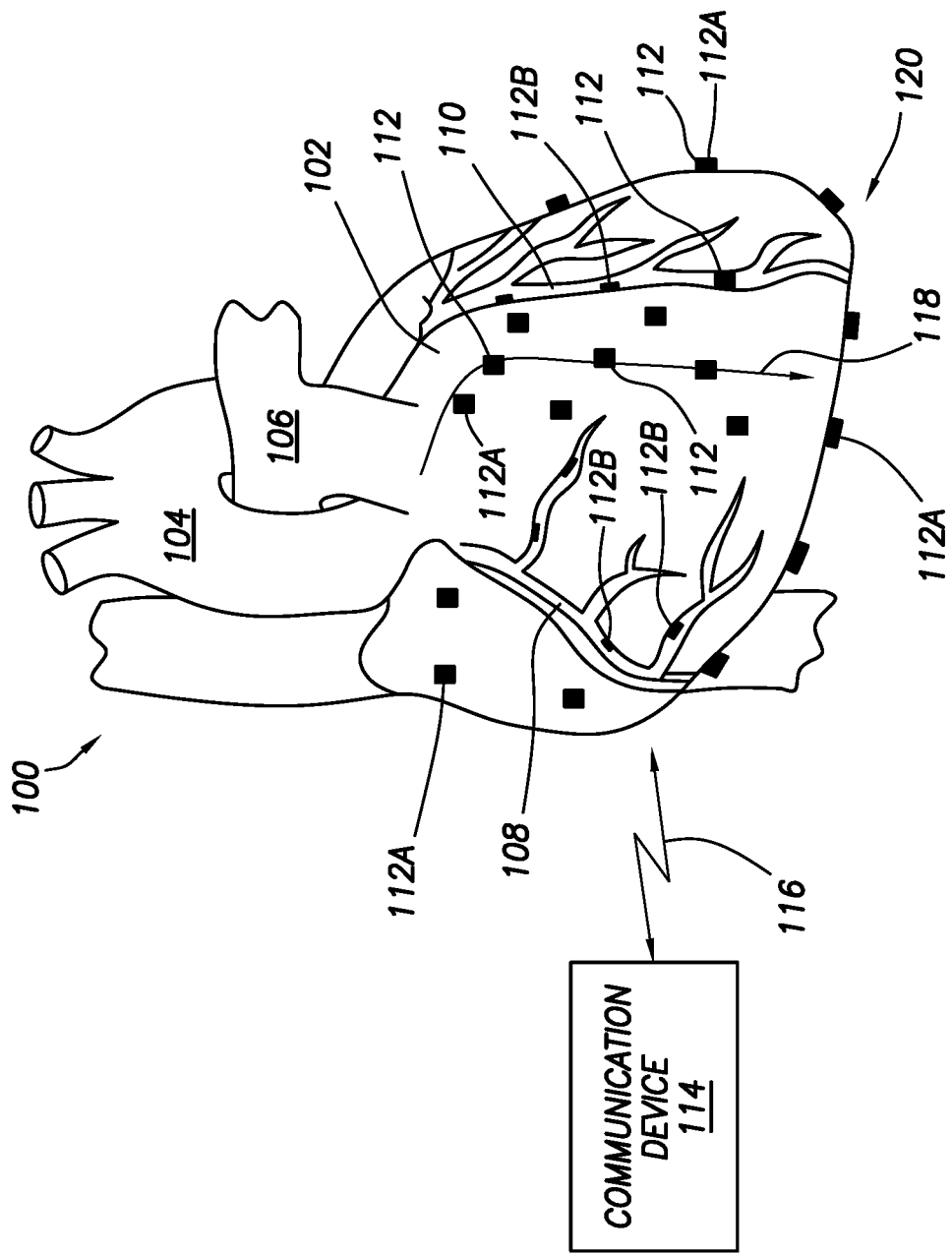
FIG. 1 shows a partial perspective, partial block diagram, view of a system for treating arrhythmias in accordance with at least some embodiments.

FIG. 1 shows a partial perspective, partial block diagram, view of a system for treating arrhythmias in accordance with at least some embodiments. In particular, visible in FIG. 1 is a heart 100 made up of heart tissue 102. Visible in the simplified view of heart 100 of FIG. 1 are the aorta 104, the pulmonary artery 106, the right coronary artery 108, left coronary artery 110, and various other arteries and veins not specifically numbered. Attached to the heart tissue 102 are a plurality of microchip devices 112. FIG. 1 illustrates several, but not all, of the placement options for the microchip devices 112 in accordance with example systems. For example, some microchip devices 112 may be coupled to the exterior of the heart 100 (i.e., epicardial placement) such that the microchip devices 112 externally abut the heart tissue (e.g., microchip devices 112A, not all epicardially placed microchip devices numbered). Further, microchip devices 112 may be placed within veins or arteries of the heart, such as the microchip devices 112B shown in the right coronary artery 108 and left coronary artery 110. Further placement options are discussed with respect to FIG. 2.

Figure 2:
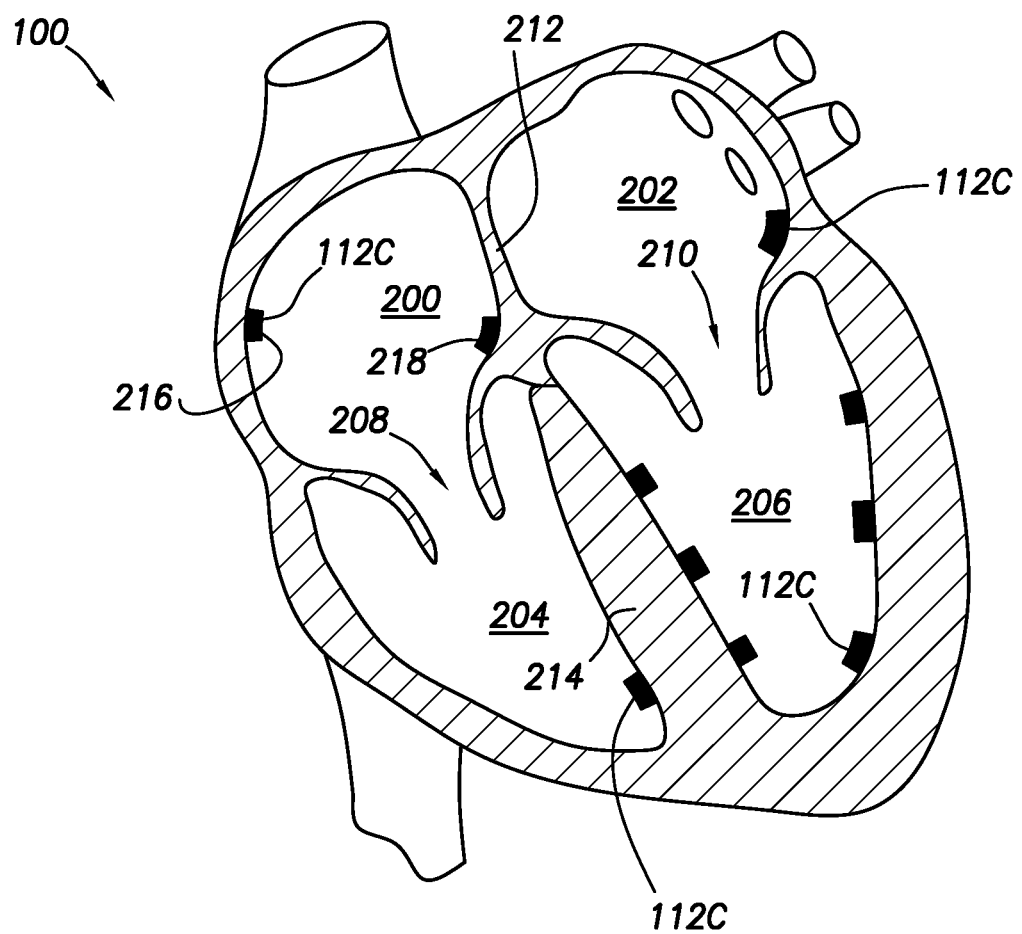
FIG. 2 shows a simplified cross-sectional view of a heart, including placement of microchip devices, in accordance with at least some embodiments.

FIG. 2 shows a simplified cross-sectional view of heart 100, including placement of microchip devices 112, in accordance with at least some embodiments. In particular, visible in FIG. 2 are the right atrium 200, the left atrium 202, the right ventricle 204, and the left ventricle 206. Further, shown in the open positions are the tricuspid valve 208 and mitral valve 210. Separating the various chambers are the atrial septum 212 and the ventricular septum 214. Some microchip devices 112 may be coupled as shown to the interior of the heart 100 (i.e., endocardial placement) such that the microchip devices 112 internally abut the heart tissue (e.g., microchip devices 112C, not all endocardially placed microchip devices numbered). The microchip devices may be placed at various locations of the right and left atria, right and left ventricles, or a combination thereof (in addition to or in place of the epicardial placement). The example microchip devices 112 in the right atrium 200 may involve placement in close proximity to or directly to the sinoatrial (SA) node (e.g., microchip device 216) that sources electrical impulses to cause the right atrium 200 and left atrium 202 to contract, and further may involve placement in close proximity to or directly to the atrioventricular (AV) node (e.g., microchip device 218) that sources electrical impulses to cause the right ventricle 204 and left ventricle 206 to contract.

A bit more technically described then, in accordance with various embodiments microchip devices may be placed at any suitable location either epicardially or endocardially. The locations include placement in the coronary venous system (e.g., coronary sinus, middle cardiac vein, left posterior ventricular vein, left marginal vein, Vein of Marshall, anterior interventricular vein or the like), coronary arterial system, or combinations. In some embodiments, placement of the microchip devices 112 may include deploying in an arrangement within the vasculature, such that much of the left ventricle and a portion of the left atrium is covered, enabling epicardial pacing and defibrillation. The microchip devices may be deployed along the length of the coronary sinus and/or its branches and anchored in position for long-term use. The microchip devices 112 may be deployed along the length of the Vein of Marshall and anchored in position for long-term use. However, not all the noted placements need be used in every case.

Returning to FIG. 1, in accordance with example systems the microchip devices 112 (regardless of placement) do not have batteries; rather, the microchip devices 112 in accordance with various embodiments have energy harvesting circuits that extract electrical energy from energy propagating proximate to each microchip device 112 (hereafter "ambient energy"). The ambient energy could take many forms. For example, the communication device 114 (or other devices and systems) may send electromagnetic waves through the body that intersect the location of the microchip devices 112. In other cases, the communication device 114 (or other devices and systems) may induce electrical current flow through the body that flows proximate to the microchip devices 112. In yet still other cases, the communication device 114 (or other devices and systems) may launch acoustic energy toward the microchip devices 112. In yet still other cases, the microchip devices 112 may harvest ambient energy directly from the heart, such as from electrical impulses generated and sourced by the heart 100 (e.g., during periods of time when the electrical system of the heart is working properly). Various example structures for harvesting ambient energy are discussed more below.

The example system further comprises communication device 114. Communication device 114 is communicatively coupled to the microchip devices 112. In particular, the communication device 114 in example embodiments is wirelessly coupled to the microchip devices 112, as illustrated by double-headed arrow 116. Various mechanisms for wireless communication between the communication device 114 and the microchip devices 112 are discussed more below. Suffice it to say at this stage that the communication device 114 may communicate individually to the microchip devices 112, and may also communicate to the microchip devices 112 as a group. The communication device 114 may take many forms. In some cases the communication device 114 resides outside the body containing the heart 100, and is physically placed abutting or proximate to the patient's skin. In other cases, the communication device 114 may be implanted under the patient's skin, such as subcutaneous placement between ribs of the patient. In yet still other cases, the functionality of the communication device 114 may be divided between a subcutaneously placed portion and an external portion, with the two portions communicatively coupled.

In example systems the communication device 114 controls the microchip devices 112. More particularly, the communication device 114 commands some or all the microchip devices 112 to apply electrical energy to the heart 100 to treat arrhythmias in the heart tissue. Consider, for example, the case of performing a defibrillation of the heart 100 (e.g., to treat an atrial fibrillation). In example defibrillation some or all the microchip devices 112 apply electrical energy to the heart tissue substantially simultaneously. Related-art defibrillation, both externally applied and internally applied, involves creating a large electrical field gradient across the heart (e.g., greater than 5V/cm). The energy needed for related-art defibrillation to be successful is generally above the pain threshold of 1 Joule (one Joule being the dissipation of one Watt for one second). Generation of such an electrical field and applying such energy in the related-art causes significant pain and trauma for the patient, damage to the myocardium, and in the case of defibrillation by implanted devices significantly reduced battery life. However, in accordance with example embodiments using a plurality of microchip devices 112 (e.g., ten or more, in some cases between 10 and 20), each microchip device 112 simultaneously applying a small and localized amount of energy together can provide sufficient overall energy to successfully perform defibrillation well below the pain threshold for the patient, thus reducing trauma for the patient and damage to the myocardium. For example, a defibrillation using the plurality of microchip devices 112 in proper placement (e.g., in and/or around the atrium) may be able to successfully defibrillate with between 0.07 and 0.8 Joules of energy.

Commanding the microchip devices 112 to apply energy substantially simultaneously can take many forms. In some cases, the communication device 114 may send a group message to all the microchip devices 112 simultaneously, the group message indicating that each device should apply energy immediately, or at a predetermined amount of time after the receiving the message (e.g., one millisecond). Considering that the distance between communication device 114 and each microchip device 112 will not be the same, the result may be slight differences in the start time of the application of energy, but given speed of propagation electromagnetic waves nevertheless would likely be within a few microseconds of each other. In other cases, each microchip device 112 is individually addressable by the communication device 114, and thus the commanding a defibrillation by the communication device 114 may involve communicating individually with each microchip device 112 and commanding application of energy. Even in the case of individually communicating with the microchip devices 112, the application of energy by each will still be within a few hundred microseconds—which on the time scale of electrical impulses of the heart is simultaneous. Thus, "substantially simultaneously" in the context of microchip devices applying electrical energy shall mean the microchip devices starting the application of energy to the heart tissue within 200 microseconds.

Pacing, on the other hand, involves applying electrical energy to the heart in such a way as to mimic electrical impulse propagation through the heart tissue. Pacing can be beneficial for hearts that experience bradycardia (i.e., heart beating slower than normal) and tachycardia (i.e., heart beating faster than normal when at rest). Moreover, many hearts have scar tissue along the path of the electrical impulses, where the scar tissue may slow or block flow of electrical impulses through the heart, and pacing using a string or array of microchip devices may be beneficial for addressing issues associated with the electrical impulses and these scar tissue areas, such as re-entrant ventricular arrhythmias. The pacing across scar tissue is sometimes referred to as normalization of conduction velocity.

Thus, pacing involves a plurality of microchip devices 112 each applying electrical energy to the heart tissue, but for pacing the application is sequentially along a predefined path that includes or intersects the microchip devices 112. Still referring to FIG. 1, an example pacing path is shown by arrow 118, which corresponds to the path along the right and left bundle branch of the conduction system of the heart. Thus, in accordance with example embodiments, pacing may be implemented by microchip devices sequentially applying electrical energy to the heart tissue along pacing path 118 over time starting near the pulmonary artery 106 and progressing downward toward the apex 120 of the heart. While the example pacing path 118 is shown to intersect only three microchip devices in the view of FIG. 1, more microchip devices may be present along the pacing path, and the pacing path may have a width (not specifically shown) that thus implicates a swath of microchip devices (e.g., the closest microchip devices on each side of the pacing path 118 of FIG. 1). In some cases, the pacing path 118 may not only include the anterior side of the heart as shown in FIG. 1, but also include continuation paths on the posterior side of the heart (not visible in FIG. 1). Alternately, the pacing path 118 may be relatively short, pacing across an area of the heart with conduction anomalies (e.g., a conduction path just across scar tissue of the heart, or across a bundle branch block).

Commanding the microchip devices 112 to apply energy sequentially along the example pacing path 118 may rely on each microchip device 112 being individually addressable by the communication device 114 as discussed above. That is, commanding a pacing action by the communication device 114 may involve communicating individually and sequentially with each microchip device 112 along the pacing path and commanding application of energy. The speed of propagation of an electrical impulse along the heart muscles is very slow considered against, for example, the speed of propagation of electromagnetic waves even in the conductive environment of the body. Thus, the communication device 114 has sufficient time to individually address each microchip device 112 along the example pacing path 118 so as to apply a piecewise continuous pacing of electrical energy to the heart along any appropriate pacing path needed by the patient.

As mentioned above, some example microchip devices 112 may have the ability to sense electrical impulses sourced by and propagating within the heart. Example structures and systems to sense electrical impulses are discussed more below. Thus, in addition to or in place of applying electrical energy to the heart for purposes of defibrillation or pacing, a microchip device 112 may sense electrical impulses propagating through heart tissue. Sensing electrical impulses may trigger the microchip device 112 to wirelessly send a message to the communication device 114 responsive to the electrical impulses. In some embodiments the message sent wirelessly to the communication device 114 may be an indication that an electrical impulse was detected in a Boolean sense. In other cases, the message sent wirelessly to the communication device 114 may be an indication of the strength of the electrical impulses as measured (again, measuring techniques for electrical impulses discussed more below).

Regardless of the type of information sent in the message wirelessly between the microchip device 112 and the communication device 114 regarding the electrical impulses in the heart, the communication device 114 may utilize the information as part of a defibrillation and/or pacing action. For example, consider a microchip device located electrically upstream of scar tissue of the heart where the scar tissue blocks or significantly reduces the flow of electrical impulses in the heart tissue. In one example system, when the communication device 114 receives the indication from the microchip device about the electrical impulses, at an appropriate time thereafter the communication device 114 individually addresses and commands microchip devices electrically downstream of the scar tissue to apply pacing energy to the heart to trigger a continuance of the electrical impulse through the heart. The specification now turns to a description of example microchip devices 112.

Figure 3:
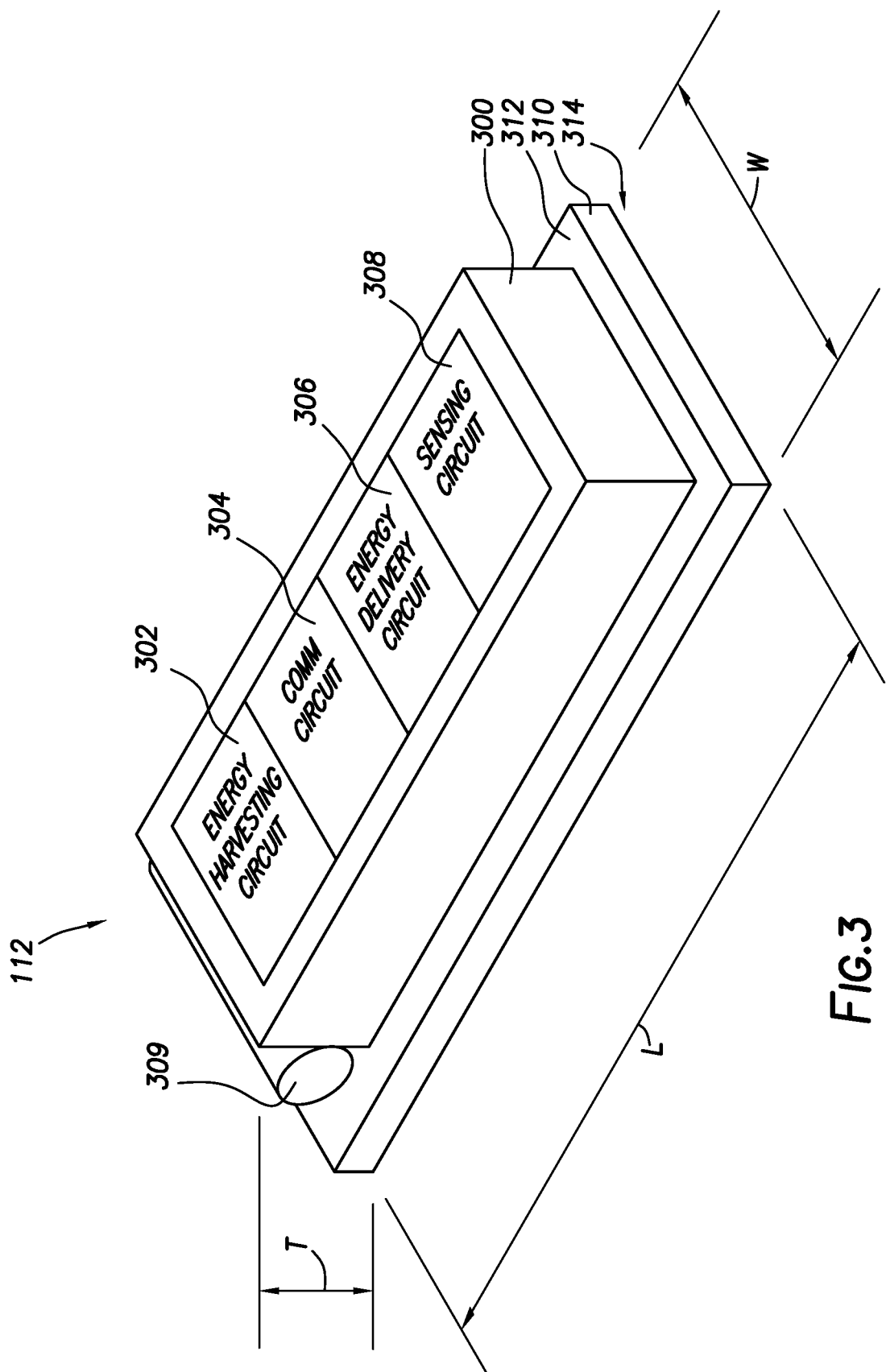
FIG. 3 shows a perspective view of a microchip device in accordance with at least some embodiments.

FIG. 3 shows a perspective view of a microchip device 112 in accordance with example embodiments. In particular, visible in FIG. 3 is a substrate 300 of semiconductor material, such as silicon. Constructed on the substrate, using semiconductor manufacturing techniques, are various circuits shown in block diagram form and conceptually divided into an energy harvesting circuit 302, a communication circuit 304, an energy delivery circuit 306, and a sensing circuit 308. The circuits are discussed in greater detail below. Further visible in FIG. 3 is a capacitor 309 associated with the substrate 300. In the example case of FIG. 3, the capacitor 309 is shown as a distinct device mechanically coupled to the substrate 300, but in other cases the capacitor 309 may be constructed directly on the substrate 300, or the functionality of the capacitor 309 may be implemented by capacitance constructed on the substrate 300 in combination with a distinct capacitor associated with the substrate as shown in FIG. 3.

Both the capacitor 309 and the substrate 300 are mechanically coupled to an anchoring structure 310. The example anchoring structure 310 is made of any suitable biocompatible material that, for reasons discussed more below, has low conductivity yet sufficient structural strength and rigidity to support the substrate 300 and various other structures. The capacitor 309 and substrate are mechanically coupled to a first side 312 of the anchoring structure 310 opposite a bottom or second side 314 of the anchoring structure 310. While the various circuits 302, 304, 306, and 308 are shown on an upper or exposed side of the substrate 300, in some cases the substrate 300 may be mounted to the anchoring structure 310 in a "flip-chip" form with the circuits facing the first side 312 of the anchoring structure. An arrangement in "flip chip" form may protect the circuits during installation and use, and may also help facilitate electrical connections to various sets of electrodes and sets of conductive pads (discussed more below).

The energy harvesting circuit 302 is defined on the substrate and is electrically coupled to the capacitor 309. The energy harvesting circuit 302 is configured to extract electrical energy from energy propagating proximate the microchip device and to store electrical energy on the capacitor 309. Electrical energy stored on the capacitor 309 thus provides operational power to the remaining circuits of the example microchip device 112. The communication circuit 304 is defined on the substrate 300 and is electrically coupled to the energy harvesting circuit 302, from which the communication circuit 304 is provided power. The communication circuit 304 is configured to receive commands originating external to the microchip device 112, such as from the communication device 114 (FIG. 1). In some cases, the communication circuit 304 may send messages to the communication device 114, such as messages indicating the presence and/or strength of electrical impulses within the heart sensed by the sensing circuit 308. The energy delivery circuit 306 is defined on the substrate 300 and is electrically coupled to a set of electrodes (the set of electrodes discussed below). The energy delivery circuit 306 is also electrically coupled to the energy harvesting circuit 302, from which the energy delivery circuit 306 is provided operational power as well as electrical energy to defibrillate and/or pace the heart. Further, the energy delivery circuit 306 is communicatively coupled to the communication circuit 304, from which the energy delivery circuit 306 may receive commands to provide or apply electrical energy to the heart tissue across the set of electrodes responsive to the commands. The sensing circuit 308 is defined on the substrate 300, is electrically coupled to the energy harvesting circuit 302, and is communicatively coupled to the communication circuit 304. The sensing circuit 308 is configured to sense electrical impulses propagating through the heart tissue, and configured to trigger the communication circuit 304 to send a message responsive to the electrical impulses propagating through the heart tissue.

FIG. 3 shows an example microchip device 112 having both the ability to sense electrical impulses sourced by and propagating within the heart tissue, and also provide electrical energy to defibrillate and/or pace the heart. However, in other example cases a microchip device 112 may have only sensing capability, and thus such a microchip device would omit the energy delivery circuit 306, and possibly implement lower overall capacitance for storage of harvested energy. Microchip devices 112 that implement sensing only may nevertheless be deployed with microchip devices 112 that implement energy delivery for purposes of the defibrillation and/or pacing. Further still, other example microchip devices may have only energy delivery capability, and thus such microchip devices would omit the sensing circuit 308. Microchip devices 112 that implement energy delivery and not sensing may nevertheless be deployed with microchip devices 112 that implement sensing such that the communication device 114 (FIG. 1) receives indications of electrical impulses sourced by and propagating within the heart, and can command other microchip devices to deliver electrical energy for purposes of defibrillation and/or pacing. The discussion that follows assumes an example microchip device with both sensing and energy delivery capability (thus implementing both the energy delivery circuit 306 and the sensing circuit 308), but such an assumption shall not be read to require both circuits in every microchip device.

The example microchip device 112 of FIG. 3 defines a length L, a width W, and a thickness T. In some example cases, the largest dimension (which could be any of the recited dimensions, though most likely the length L), is 10 millimeters or less, and in some cases one millimeter. In some cases, the length and width may each be about one millimeter, and as will be shown below having a microchip device in the recited ranges enables placement directly within the coronary artery system or coronary vein system.

Figure 4:
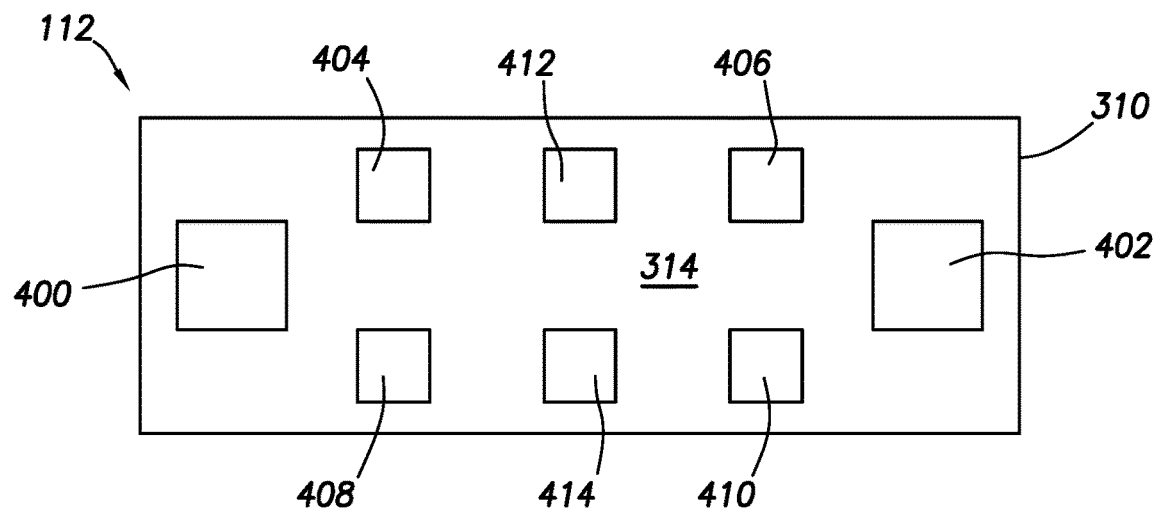
FIG. 4 shows a bottom view of the example microchip device in accordance with at least some embodiments.

FIG. 4 shows a bottom view of the example microchip device 112 in accordance with at least some embodiments. In particular, visible in FIG. 4 is the second or bottom side 314 of the anchoring structure 310. Disposed on the bottom side 314 of the anchoring structure 310 is a set of electrodes comprising a first electrode 400 and a second electrode 402. The electrodes 400 and 402 are metallic material that may be placed or deposited on the bottom side 314 of the anchoring structure 310 in any suitable form. In some example cases, the electrodes 400 and 402 are made of platinum, iridium, or titanium, but any metallic material suitable for extended use within the body (and abutting heart tissue) may be used. In the example system, the set of electrodes comprising electrode 400 and 402 are electrically coupled to the energy delivery circuit 306 (not shown in FIG. 4), and across which the microchip device 112 applies electrical energy to the heart tissue for defibrillation and/or pacing.

Further visible in the view of FIG. 4 is a set of conductive pads comprising conductive pads 404 and 406. The conductive pads 404 and 406 are metallic material that may be placed or deposited on the bottom side 314 of the anchoring structure 310 in any suitable form. In some example cases, the conductive pads 404 and 406 are made of platinum, iridium, or titanium, but any metallic material suitable for extended use within the body (and abutting heart tissue) may be used. In the example system, the set of conductive pads comprising conductive pads 404 and 406 are electrically coupled to the energy harvesting circuit 302 (not shown in FIG. 4), and across which the microchip device 112 may extract electrical energy in some embodiments. In other cases, discussed more below, electrical energy is harvested by the energy harvesting circuit from ambient energy in the form of electromagnetic waves, and thus conductive pads 404 and 406 may be omitted.

Further visible in the view of FIG. 4 is a set of conductive pads comprising conductive pads 408 and 410. The conductive pads 408 and 410 are metallic material that may be placed or deposited on the bottom side 314 of the anchoring structure 310 in any suitable form. In some example cases, the conductive pads 408 and 410 are made of platinum, iridium, or titanium, but any metallic material suitable for extended use within the body (and abutting heart tissue) may be used. In the example system, the set of conductive pads comprising conductive pads 408 and 410 are electrically coupled to the sensing circuit 308 (not shown in FIG. 4), and across which the microchip device 112 may sense electrical impulses sourced by and propagating in the heart tissue. Other example microchip devices 112 either omit the sensing circuit, or sense in a different way (discussed more below), and thus conductive pads 408 and 410 may be omitted.

Further visible in the view of FIG. 4 is a set of conductive pads comprising conductive pads 412 and 414. The conductive pads 412 and 414 are metallic material that may be placed or deposited on the bottom side 314 of the anchoring structure 310 in any suitable form. In some example cases, the conductive pads 412 and 414 are made of platinum, iridium, or titanium, but any metallic material suitable for extended use within the body (and abutting heart tissue) may be used. In the example system, the set of conductive pads comprising conductive pads 412 and 414 are electrically coupled to the communication circuit 304 (not shown in FIG. 4), and across which the microchip device 112 induce electrical current flow as an alternate communication system between the microchip device 112 and the communication device 114. Other example microchip devices 112 may communicate with the communication device 114 solely using electromagnetic waves, and thus conductive pads 412 and 414 may be omitted.

The example anchoring structure 310 is a non-conductive element, and thus the electrodes and conductive pads are electrically isolated from the standpoint of the anchoring structure. Electrical connections between the electrodes (or conductive pads) and their respective circuits (e.g., energy harvesting circuit 302, energy delivery circuit 306, and sensing circuit 308) may be made through holes or vias through the anchoring structure 310 to electrically couple to connection pads defined on the substrate 300 (not shown). In some cases, the anchoring structure may be a multi-level structure with electrical traces disposed on interposed layers to align the traces for electrical contact with the various circuits of the substrate 300.

The various microchip devices 112 discussed to this point are configured for placement to abut the heart tissue by way of a carrier structure to which a plurality of the microchip devices 112 is mechanically coupled. Stated otherwise, a carrier structure having a plurality of microchip devices may be used to place and hold each of the plurality of microchip devices 112 to abut the heart tissue at respective locations. The specification now turns to example carrier structures.

Figure 5:
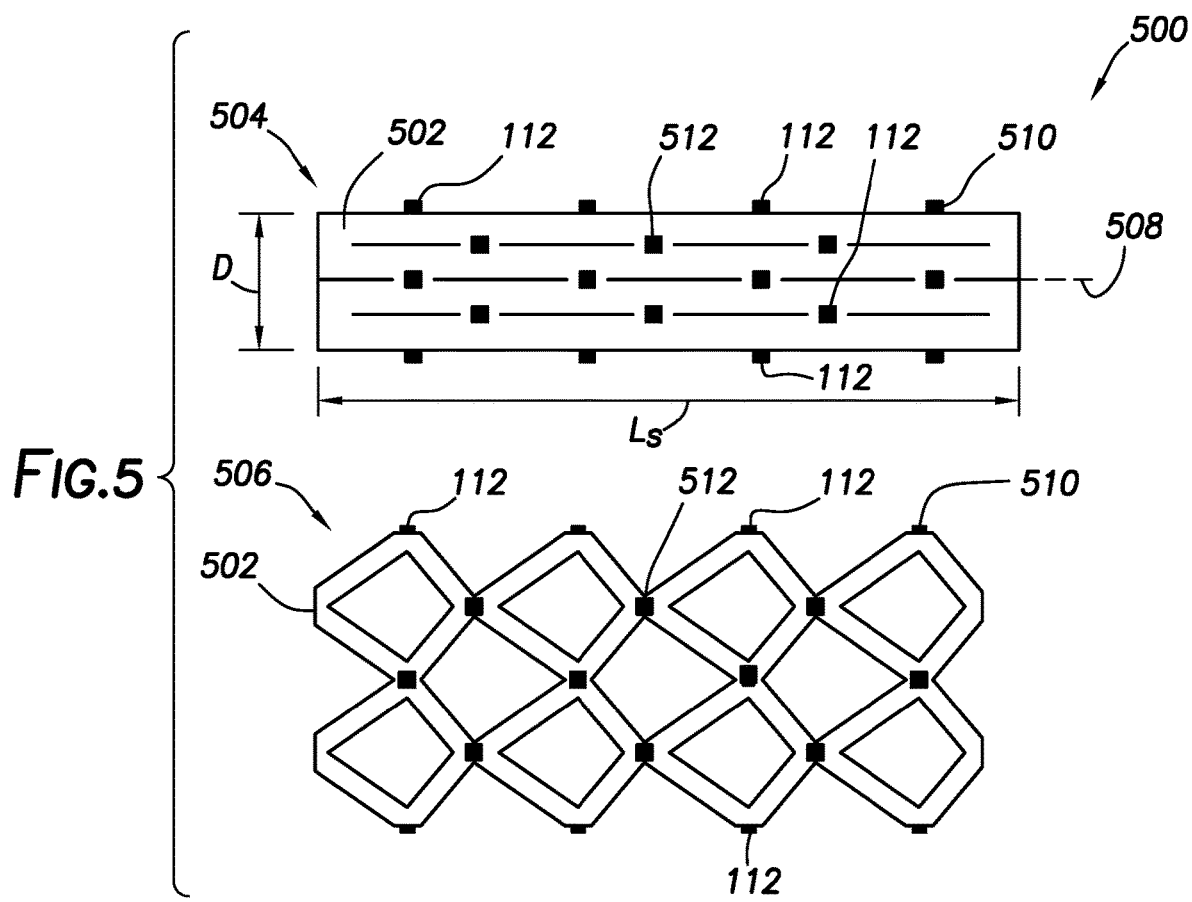
FIG. 5 shows two elevational views of stent-based placement of microchip devices in accordance with at least some embodiments.

FIG. 5 shows two elevational views of stent-based placement of microchip devices in accordance with at least some embodiments. In particular, FIG. 5 shows a carrier structure 500 in the form of a stent 502 of metallic material. The upper drawing 504 of FIG. 5 shows the stent 502 prior to expansion (i.e., prior to final placement), and the lower drawing 506 shows the stent 502 after expansion (e.g., after expansion by way of a balloon catheter). Referring initially to the upper drawing 504, the example stent 502 has a longitudinal axis 508 and a length Ls (e.g., the length Ls could be between one and two centimeters, inclusive). Stents are generally tubular devices and thus define a diameter D in the un-expanded state small enough to fit, for example, within portions of the coronary artery system (e.g., the left and right coronary arteries). A plurality of microchip devices 112 are mechanically coupled to the stent 502 at spaced apart locations along the longitudinal axis 508 of the stent. Moreover, considering that the stent 502 is a tubular structure, the microchip devices are also placed at varying and distinct radial locations along the longitudinal axis 508 of the stent 502. For example, microchip device 510 is at a different location along the longitudinal axis 508 than microchip device 512, and microchip device 510 is also at a different and distinct radial location than microchip device 512.

The microchip devices 112 may be coupled to the stent 502 in any suitable form. For example, the microchip device 112 may be adhered to the metallic structure such that the bottom sides 314 of anchoring structures 310 (not visible in FIG. 5) face outward relative to the longitudinal axis 508. In this way, once expanded (discussed more immediately below), the electrodes and conductive pads may be held to abut the heart tissue, and thus be electrically coupled to the heart tissue.

Referring now to the lower drawing 506 of FIG. 5, once in place and expanded (e.g., by a balloon catheter), the carrier structure 500 in the form of stent 502 presses and holds the microchip devices against the walls of the vein or artery of the heart, thus placing the microchip devices into an abutting relationship with the heart tissue, in this case while enabling blood flow through the central aperture along the longitudinal axis 508. Rather than placement to open a vein or artery, the stent 502 may be placed to span a portion of the heart tissue experiencing conductivity issues (e.g. scar tissue). The microchip devices 112, under command of the communication device 114 (FIG. 1), may pace the electrical impulses of the heart across the portion experiencing conductivity issues. The stent 502 may also serve dual duty, holding open an otherwise blocked vein or artery, and also placing and holding microchip devices 112 in place to abut the heart tissue.

Placing and expansion of the carrier structure 500 in the form a stent 502 may use now existing or after-developed technology for placement of stents. For example, the un-expanded stent 502 may be carried on or within the distal end of a catheter system and placed as needed within the coronary artery system. Once in place, a balloon catheter may be inflated to bend and expand the metallic material of the stent 502, and then the balloon deflated and the catheter removed leaving the stent 502 and the plurality of microchip devices 112 in place.

Figure 6:
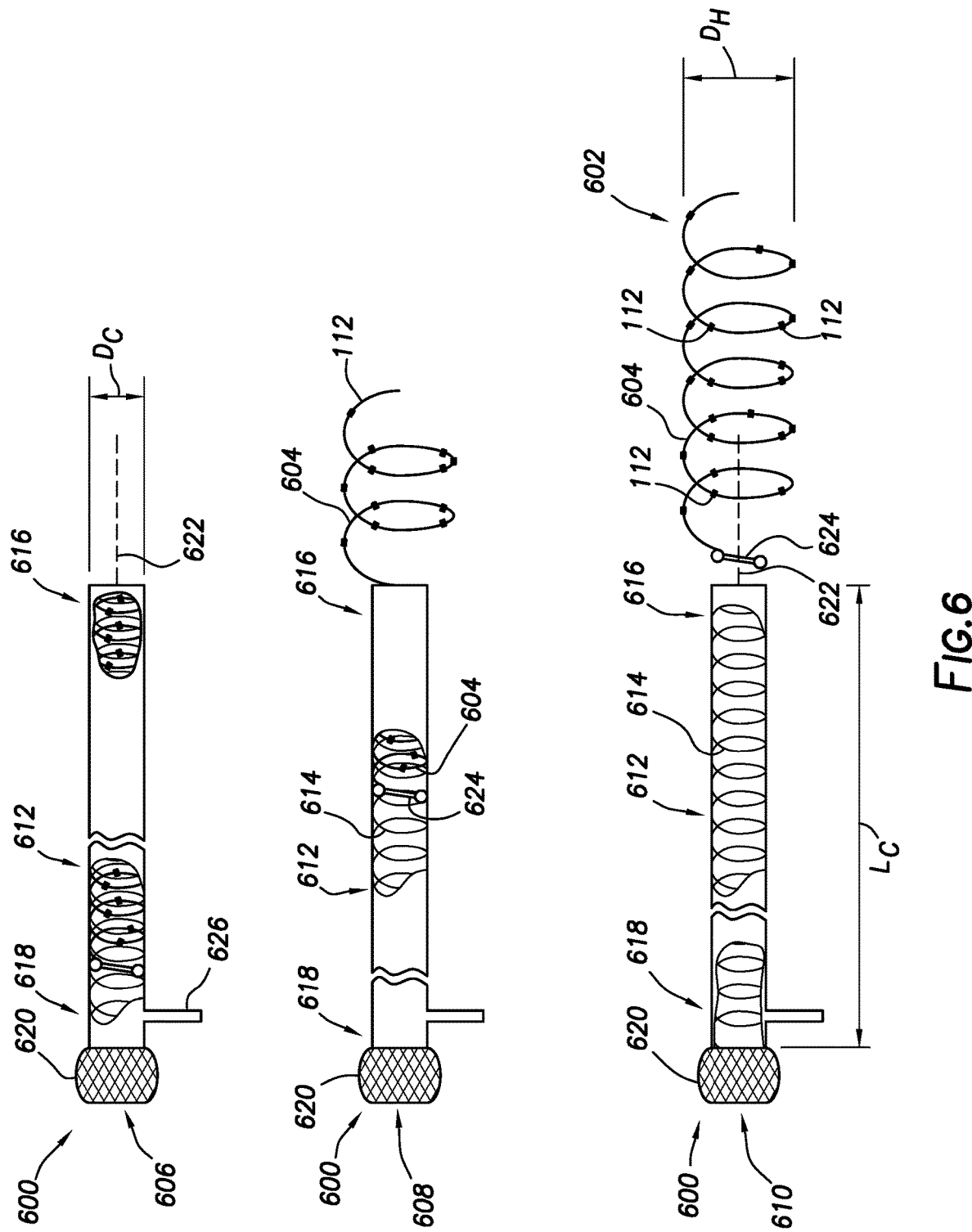
FIG. 6 shows three elevational views of a microchip device placement system and method in accordance with at least some embodiments.

FIG. 6 shows three elevational views of a microchip device placement system and method in accordance with at least some embodiments. In particular, FIG. 6 shows a catheter system 600 for delivery of a carrier structure 602 in the form of a spring or helical wire 604 having a plurality of microchip devices 112 attached thereto. The upper drawing 606 shows the catheter system 600 in an initial state with the helical wire 604 and microchip devices 112 carried fully therein. The middle drawing 608 shows the catheter system 600 with the helical wire 604 and microchip devices in a partially deployed state, and the lower drawing 610 shows the catheter system 600 with the helical wire 604 and microchip devices 112 fully deployed.

Referring initially to the lower drawing 610 (though the elements introduced with respect to the lower drawing 610 are equally applicable to the middle and upper drawings). The catheter system 600, shown in partial cutaway view, comprises a catheter 612 that defines an internal lumen with an internal volume along the length $L_C$ of the catheter 612. The catheter 612 is of sufficient length for delivery into the coronary veins and/or arteries in a similar fashion to the delivery of stents discussed above. Disposed within the catheter 612 is a helical wire or spring 614 that has a diameter that abuts the inside diameter of the catheter 612 and extends along substantially the entire length $L_C$ of the catheter 612. The spring 614 terminates on the distal end 616 proximate a distal aperture of the lumen of the catheter 612. On the proximal end 618 the spring 614 mechanically couples to a knurled knob 620. Thus, turning of the knurled knob 620 results in rotation of the spring 614 within the catheter 612, the rotation about a longitudinal axis 622 of the spring 614 (which longitudinal axis 622 is coaxial with the longitudinal axis of the catheter 612). The carrier structure 602 in the example embodiments of FIG. 6 is a spring or helical wire 604 whose rest diameter $D_H$ (i.e., the diameter the helical wire 604 takes when under no externally applied forces) is larger than an internal diameter $D_C$ of the catheter 612. It follows that prior to being loaded into the catheter 612, and after being deployed out of the catheter 612, the helical wire 604 takes on a diameter larger than the diameter $D_C$ of the catheter, and in most cases the helical wire will abut the inside diameter or inside surface of a vein or artery into which the helical wire 604 and microchip devices 112 thereon have been deployed. On a proximal end of the helical wire 604 resides a displacement structure 624.

The lower drawing 610 of FIG. 6 shows the carrier structure 602 in the form of a helical wire 604 fully deployed out of the catheter 612 (as we shall see, by turning of the knurled knob 620). Thus, the view of the lower drawing 610 is either: prior to loading the helical wire 604 within the catheter 612; or with the helical wire 604 fully deployed in a vein or artery (e.g., coronary artery system) and just prior to removal of the catheter 612. Once in place, the carrier structure 602 in the form of helical wire 604 presses and holds the microchip devices 112 against the walls of the vein or artery of the heart, thus placing the microchip devices into an abutting relationship with the heart tissue. As with some of the stent embodiments of the carrier structure, rather than placement to open a vein or artery, the helical wire 604 may be placed to span a portion of the heart tissue experiencing conductivity issues (e.g., scar tissue), and thus the microchip devices 112, under command of the communication device 114 (FIG. 1), may pace the electrical impulses of the heart across the portion experiencing conductivity issues.

Still referring to FIG. 6, particularly the middle drawing 608. The middle drawing 608 shows the catheter 612 in partial cutaway view to show operation of the displacement structure 624. In particular, the displacement structure 624 is designed and constructed to be placed within the internal diameter of the catheter 612, and more particularly to reside in the spaces between coils of the spring 614. The example placement structure appears as a "bar bell" shape, with two spherical objects disposed on opposite sides a pin or bar element; however, the displacement structure 624 may take any suitable form having distal ends that move along between coils of the spring and, as we shall see, can be pushed along by the spring 614 as the spring 614 rotates about the longitudinal central axis 622. That is, as the knurled knob 620 is turned spring 614 likewise turns or rotates about the longitudinal central axis 622. Based on the turning of the spring 614 the displacement structure 624 is translated along the longitudinal axis 622, with the direction of translation based on the direction that knurled knob 620 is turned. The spring 614 thus acts similar to a lead-screw assembly, translating the displacement structure 624 along the longitudinal axis 622. Thus, the helical wire 604 and microchip devices 112 attached to the displacement structure 624 may be "loaded" into the catheter 612 by placing the displacement structure 624 within the aperture on the distal end 616 of the catheter 612 and turning the knurled knob 620 in such a way as to pull the displacement structure 624 into the internal lumen. As the displacement structure 624 is pulled inward, so too is the helical wire 604 with the microchip devices 112 attached thereto. Pulling the helical wire 604 into the catheter 612 places the helical wire into tension, making the diameter smaller. Thus, the middle drawing 608 of FIG. 6 shows the helical wire 604 either: partially loaded into the catheter 612; or partially deployed into a vein or artery.

Now referring to the upper drawings 606 of the FIG. 6. The upper drawings 606 shows the catheter system 600 (in partial cutaway view) with the carrier structure 602 in the form of a helical wire 604 with microchip devices 112 attached thereto contained fully within the catheter 612. Thus, the upper drawing 606 shows a catheter system 600 ready to deploy a carrier structure 602 in the form of a helical wire 604, including an intraluminal flush port 626 in fluid communication with the lumen of the catheter 612, and as the name implies the intraluminal flush port 626 may be used to supply fluids (e.g., saline) to flush the catheter 612 both prior to insertion and during delivery of the helical wire 604 and microchip devices 112 attached thereto.

The microchip devices 112 may be coupled to the helical wire 604 in any suitable form. For example, the microchip devices 112 may be adhered to the helical wire such that the anchoring structures 310 (not visible in FIG. 6) face outward relative to the longitudinal axis 622 when deployed. In this way, once the helical wire is deployed out of the catheter 612 and thus expanded, the electrodes and conductive pads may be held to abut the heart tissue, and thus be electrically coupled to the heart tissue.

Figure 7:
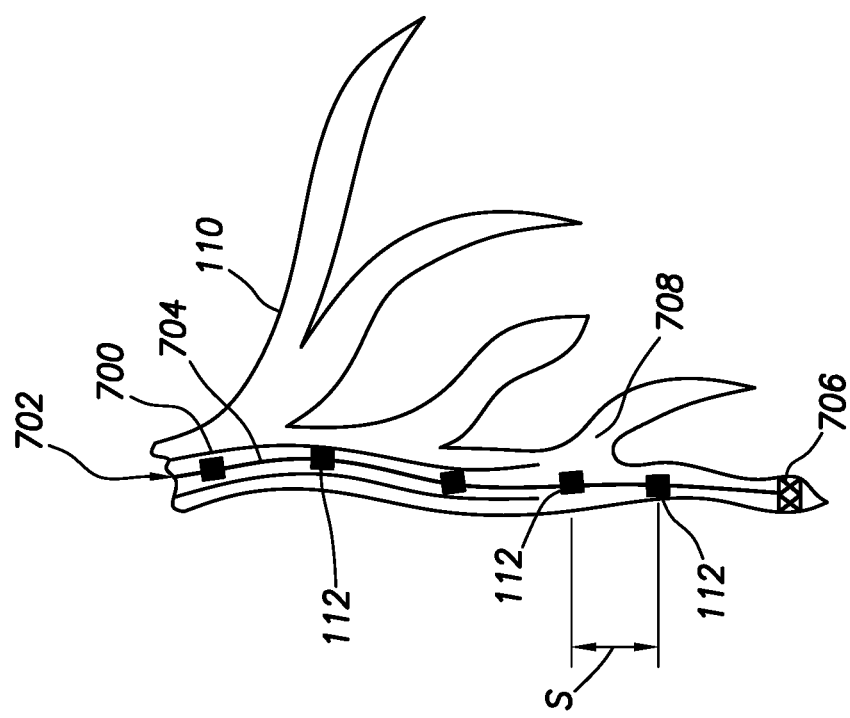
FIG. 7 shows a cutaway elevation view of a vein or artery with a carrier structure in the form of a wire in accordance with at least some embodiments.

FIG. 7 shows a cutaway elevation view of a vein or artery with a carrier structure in the form of a wire in accordance with at least some embodiments. In particular, FIG. 7 shows a portion of the left coronary artery 110. Disposed within the example coronary artery 110 is a catheter 700 that defines an internal lumen. Disposed within the internal lumen of the catheter 700 is a carrier structure 702 in the form of a metallic wire 704. Spaced along and adhered to the metallic wire 704 is a plurality of microchip devices 112. The microchip devices 112 may have any suitable spacing, and in some example cases the microchip devices 112 are spaced apart along the metallic wire 704 at a spacing S of about one centimeter. The metallic wire 704 may take any suitable form, and in one example case the metallic wire has a diameter between and including 0.4 and 0.45 millimeters. On a distal end of the metallic wire may reside an anchor structure 706. As the name implies, the anchor structure 706 mechanically anchors the distal end of the metallic wire 704 to enable further placement (e.g., to enable withdrawing the catheter 700 while paying out the metallic wire 704 and microchip devices 112). The anchor structure 706 may also lower the chances of inadvertently puncturing the artery or vein into which the metallic wire 704 and microchip devices 112 are placed.

Using the catheter 700 the metallic wire 704 and microchip devices 112 may be placed into the coronary artery or vein system. As shown, placement may begin at a distalmost end of an artery or vein, and then proceed proximally. Though not specifically shown in FIG. 7 so as not to unduly complicate the figure, once a branch location is reached (e.g., branch location 708) the catheter 700 may again be advanced distally into the new branch of the artery or vein, all the while paying out the metallic wire 704 and microchip devices 112. Thus, in these embodiments each major branch of the artery or vein may contain a loop of metallic wire 704 with microchip devices 112 (with the exception of the distal-most artery or vein containing the anchoring structure 706). Once the complete length of the metallic wire 704 with microchip devices 112 have been placed, the catheter 700 may be removed leaving microchip devices 112 held in place by the metallic wire 704. The microchip devices 112 may be coupled to the metallic wire 704 in any suitable form. For example, the microchip devices 112 may be adhered to the metallic wire such that the anchoring structures 310 (not visible in FIG. 7), when deployed, abut the heart tissue.

The various microchip devices 112 discussed in reference to FIGS. 3-7 involve use of a carrier structure to which the microchip devices 112 are attached, and the carrier structure not only enables placement but also holds the microchip devices to abut the heart tissue. These carrier structure-based systems are particularly suited for placing the microchip devices in the coronary artery system and coronary vein system. However, FIGS. 1 and 2 also discussed placement of microchip devices 112 to abut the heart tissue outside the artery or vein system, as well as within the heart chambers. Thus, the specification now turns to example microchip devices that may be mechanically and electrically coupled to abut the heart tissue, but not necessarily requiring use of the carrier structure.

Figure 8:
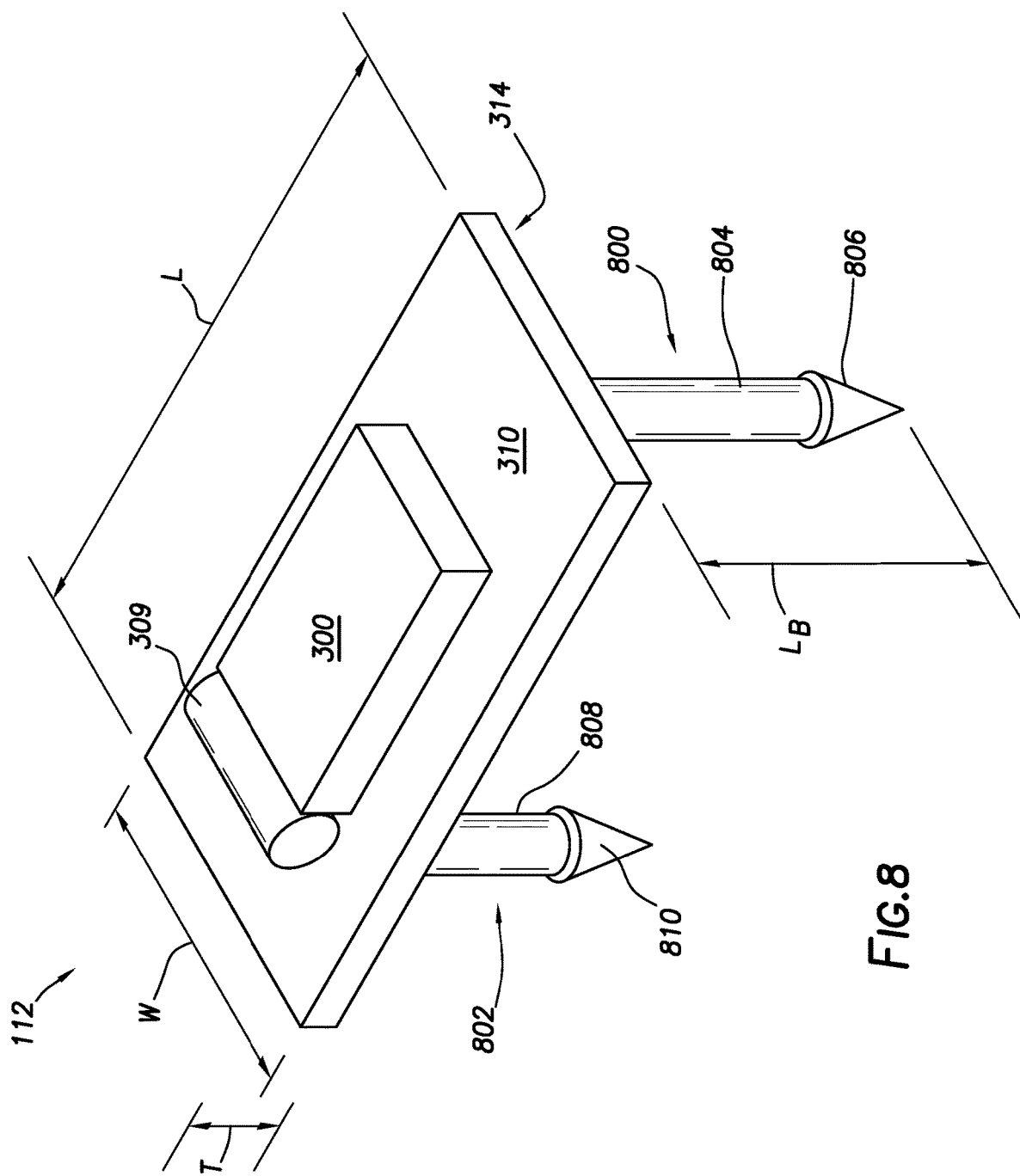
FIG. 8 shows a perspective view of a microchip device in accordance with at least some embodiments.

FIG. 8 shows a perspective view of a microchip device 112 in accordance with at least some embodiments. In particular, shown in FIG. 8 is the substrate 300 mechanically coupled to the anchoring structure 310, and also showing capacitor 309 associated with the substrate 300. The example microchip device 112 of FIG. 8 further comprises a system for mechanically coupling the microchip device 112 to the heart tissue. The system for mechanically coupling couples the microchip device 112 to the myocardium either directly, by way of the epicardium (for microchip devices epicardially located), or by way of the endocardium (for microchip devices endocardially placed). The example microchip device 112 of FIG. 8 shows the system for mechanically coupling as a set of barbed pins 800 and 802. In particular, a first pin 804 is coupled to the second side 314 of the anchoring structure 310, and the first pin 804 extends away from the anchoring structure 310 perpendicular to a plane defined by the anchoring structure 310. The pin 804 defines on a distal end thereof a barb 806 in the example form of a larger diameter portion terminating in a point, thus defining an inverted conic frustum in the view of FIG. 8. Likewise, the example system comprises a second pin 808 coupled to the second side 314 of the anchoring structure 310 and spaced apart from the first pin 804. The second pin 808 extends away from the anchoring structure 310 perpendicular to a plane defined by the anchoring structure 310. The pin 808 defines on a distal end thereof a barb 810 in the example form of a stepped larger diameter portion terminating in a point, thus defining an inverted conic frustum in the view of FIG. 8. Other barb structures (e.g., shark-fin style barbs similar to those used on fishing hooks) may be equivalently used. Thus, coupling the example microchip device 112 of FIG. 8 to the myocardium may involve pushing the microchip device 112 against the myocardium to puncture the myocardium with the barbed ends 806 and 810. Once in place, the barbs 806 and 810 hold the microchip device 112 such that the microchip device 112 abuts the heart tissue, and more particularly the bottom side 314 of the anchoring structure 310 abuts the heart tissue such that the electrodes and conductive pads electrically contact the heart tissue.

The barbed pins 800 and 802 may be made of a nitinol structure; however, other materials may include stainless steel, titanium, and tungsten. The barbed pins may have coatings (such as hydrophilic or hydrophobic coatings to provide lubrication), or may be coated with antithrombogenic material.

In some embodiments, the barbed pins 800 and 802 provide only mechanical coupling of the microchip device 112 to the heart tissue. However, in other cases the barbed pins 800 and 802 not only provide for mechanical coupling, but also electrically couple the microchip device 112 to the heart tissue. That is, in some embodiments the set of electrodes by which the energy delivery circuit 306 (not shown in FIG. 8) applies electrical energy to the heart tissue are the barbed pins 800 and 802. In such alternate embodiments the energy delivery circuit 306 electrically couples to the barbed pins 800 and 802. In yet still other cases (e.g., microchip devices that omit energy delivery and implement only sensing), the barbed pins 800 and 802 may not only mechanically couple the microchip device to the heart tissue, but may also be the conductive element by which the sensing circuit 308 couples to the heart tissue to sense electrical impulses sourced by and propagating through the heart. In such alternate embodiments the sensing circuit electrically couples to the barbed pins 800 and 802. In yet still other alternate embodiments, the barbed pins 800 and 802 may not only mechanically couple the microchip device to the heart tissue, but may also be the conductive elements by which the energy harvesting circuit 302 (not shown in FIG. 8) couples to the heart tissue to harvest electrical energy. In such alternate embodiments the energy harvesting circuit 302 electrically couples to the barbed pins 800 and 802. In yet still other alternate embodiments, the barbed pins 800 and 802 may not only mechanically couple the microchip device to the heart tissue, but may also be the conductive elements by which the communication circuit 304 (not shown in FIG. 8) couples to the heart tissue to send and receive messages. In such alternate embodiments the communication circuit 304 electrically couples to the barbed pins 800 and 802.

FIG. 8 further shows various dimensions of the example microchip device 112 comprising a mechanical structure to anchor to heart tissue in the form of barbed pins 800 and 802. In particular, visible in FIG. 8 is the length L, width W, partial thickness T (comprising the anchoring structure 310 and substrate 300), and a length $L_B$ of the barbed pins 800 and 802 (measured perpendicularly from the bottom side 314 of the anchoring structure). In some example cases the length $L_B$ of the barbed pins 800 and 802 may be from 0.1 to 2 millimeters inclusive. The largest remaining dimension (most likely the length L) in these embodiments may be 1 to 10 millimeters inclusive, in some cases between 2 and 5 millimeters inclusive. The embodiments of FIG. 8 are slightly larger than the embodiments of FIG. 3 to provide sufficient size to accommodate the barbed pins 800 and 802.

Figure 9:
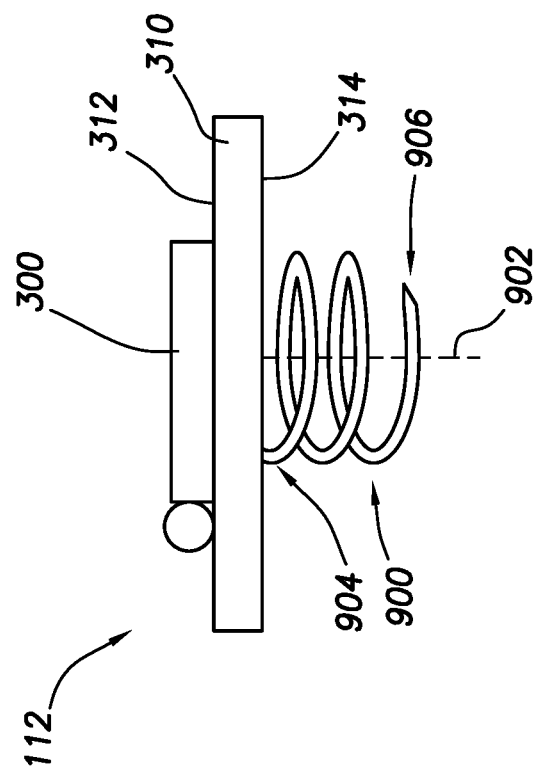
FIG. 9 shows a side elevation view of a microchip device in accordance with at least some embodiments.

FIG. 9 shows a side elevation view of a microchip device in accordance with at least some embodiments. In particular, visible in FIG. 9 is the anchoring structure 310 having the substrate 300 and capacitor 309 on the first side 312 thereof. On the bottom side 314 is defined another mechanical structure for coupling the anchoring structure 310 to abut heart tissue, the mechanical structure in the form of a helical screw 900. The example helical screw 900 has a central axis 902. In example systems, the central axis 902 intersects the anchoring structure 310 in the center thereof, but other placements are possible. It follows that a proximal end 904 of the helical screw 900 mechanically couples to the bottom side 314 of the anchoring structure 310, and the helical screw 900 extends away from the plane defined by the anchoring structure 310 along the central axis 902, the extending opposite the substrate 300.

Installation of the microchip device 112 of FIG. 9 thus involves placing the distal end 906 of the helical screw 900 against the heart tissue, and then rotating the entire microchip device 112 about the central axis 902. The distal end 906 thus punctures the endocardium or epicardium, and then proceeds to mechanically couple to myocardium.

In some embodiments, the helical screw 900 provides only mechanical coupling of the microchip device 112 to the heart tissue. However, in other cases the helical screw 900 not only provides for mechanical coupling, but also electrically couples the microchip device 112 to the heart tissue. That is, in some embodiments one electrode of the set of electrodes by which the energy delivery circuit 306 (not shown in FIG. 9) applies electrical energy to the heart tissue is the helical screw 900, with the second electrode, for example, disposed on the bottom side 314 of the anchoring structure. In such alternate embodiments the energy delivery circuit 306 electrically couples to the helical screw 900. In yet still other cases (e.g., microchip devices that omit energy delivery and implement only sensing), the helical screw may not only mechanically couple the microchip device to the heat tissue, but may also be one of the conductive elements by which the sensing circuit 308 (not shown in FIG. 9) couples to the heart tissue to sense electrical impulses sourced by and propagating through the heart. In such alternate embodiments the sensing circuit electrically couples to the helical screw 900, with the second conductive pad disposed on the bottom side 314 of the anchoring structure 310. In yet still other alternate embodiments, the helical screw 900 may not only mechanically couple the microchip device to the heart tissue, but may also be a conductive element by which the energy harvesting circuit 302 (not shown in FIG. 9) couples to the heart tissue to harvest electrical energy. In such alternate embodiments the energy harvesting circuit 302 electrically couples to the helical screw 900, with the second conductive pad disposed on the bottom side 314 of the anchoring structure 310. In yet still other alternate embodiments, the helical screw 900 may not only mechanically couple the microchip device to the heart tissue, but may also be a conductive element by which the communication circuit 304 (not shown in FIG. 9) couples to the heart tissue to send and receive messages. In such alternate embodiments the communication circuit 304 electrically couples to the helical screw 900, with the second conductive pad disposed on the bottom side 314 of the anchoring structure 310.

FIG. 9 shows no specific dimensions of the example microchip device 112; however, the length, width, partial thickness (comprising the anchoring structure 310 and substrate 300), and a length of the helical screw 900 (measured perpendicularly from the bottom side 314 of the anchoring structure) may be of similar size ranges as discussed with respect to FIG. 8. The helical screw 900 may be made of any suitable material, such as a nitinol structure; however, other materials may include stainless steel, titanium, and tungsten. The helical screw may have a coating thereon (such as hydrophilic or hydrophobic coatings to provide lubrication), or may be coated with antithrombogenic material. In some cases, the helical screw 900 may be coated with an electrically insulating material, and having only the distal end 906 electrically exposed to provide greater electrical separation between the electrode or conductive pad on the bottom side 314 of the anchoring structure 310 and the electrical coupling to the tissue at the distal end 906 of the helical screw 900. The specification now turns to various aspects of the circuits constructed on the substrate 300.

Figure 10:
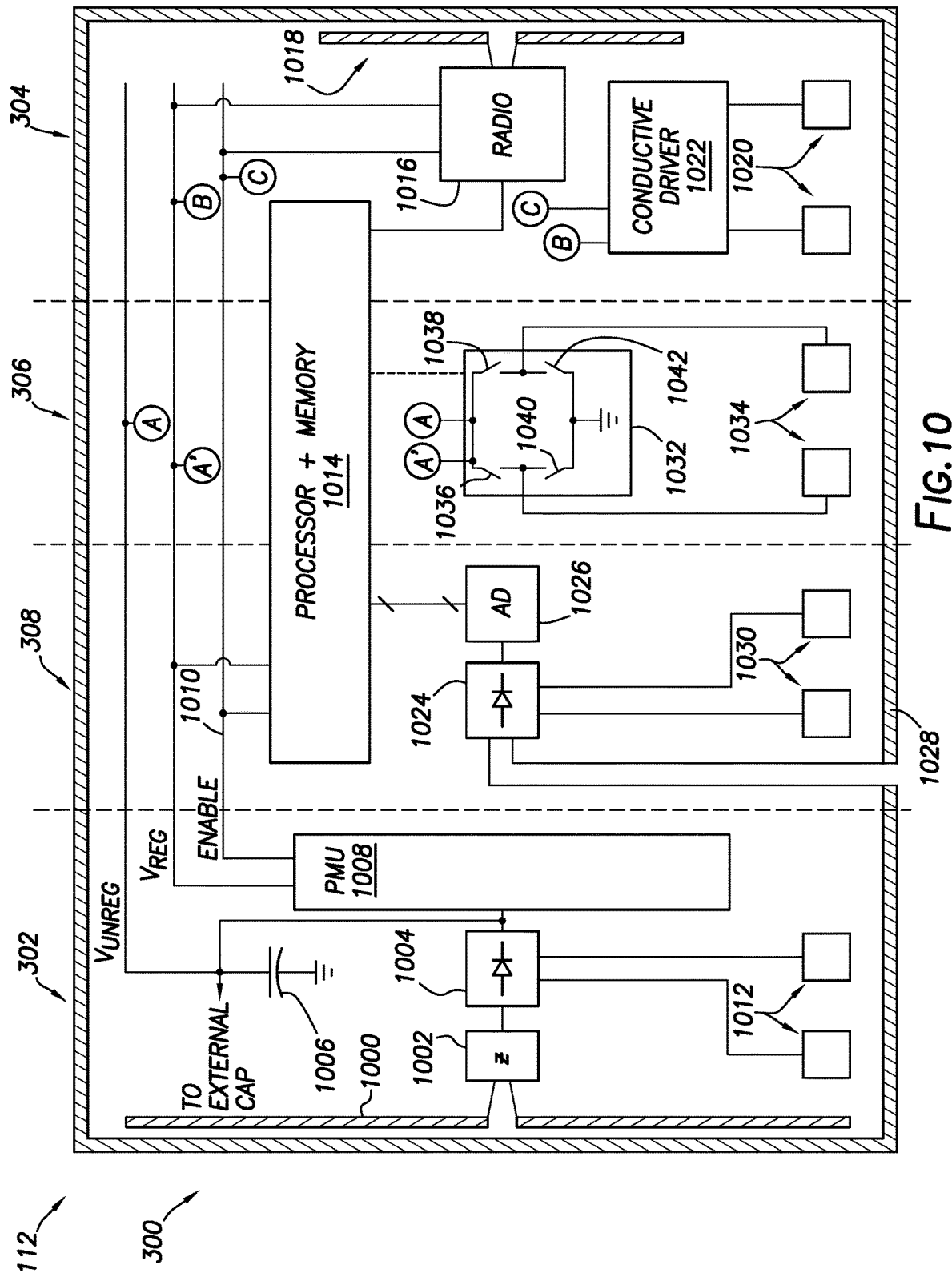
FIG. 10 shows a partial schematic, partial block diagram, view of the various circuits of the substrate in accordance with at least some embodiments.

FIG. 10 shows a partial schematic, partial block diagram, view of the various circuits of the substrate in accordance with at least some embodiments. In particular, FIG. 10 shows a set of example circuits that may be monolithically constructed on a substrate of semiconductor material, such as silicon. For purposes of description, the various circuits have been conceptually, and to some extent physically, separated in the view of FIG. 10. However, some example components are large and physically span the entire figure (e.g., the loop antenna used by sensing circuit), and some components are shared (e.g., the memory and processor) and thus the conceptual division for purposes of description shall not be read to require physical segregation in the operable microchip device 112. With the caveats in mind, FIG. 10 shows a substrate 300 of a microchip device 112 in accordance with at least some embodiments. Shown in FIG. 10 is the energy harvesting circuit 302, the communication circuit 304, the energy delivery circuit 306, and the sensing circuit 308. Each will be discussed in turn.

Considering first the energy harvesting circuit 302. In the various embodiments the microchip device 112 harvests ambient energy to provide operational power to the other devices and components on the substrate. In some cases, the microchip device 112 harvests ambient energy in the form of electromagnetic waves propagating near, around, and/or past the microchip device 112. To that end, some example energy harvesting circuits 302 implement an energy harvesting antenna 1000 illustratively shown as a dipole antenna. In example cases, the energy harvesting antenna 1000 has an operating frequency of 1 Mega-Hertz (MHz) or above, in some cases having an operating frequency of between 1 MHz and 10 GigaHertz (GHz) inclusive, and in specific cases between 100 MHz and 1 GHz inclusive. The energy harvesting antenna 1000 may be monolithically created on the substrate 300 by deposition of metallic material and selective etching to create metallic conductors. Other monolithically created antenna types may be equivalently used, such as bow tie antennas and patch antennas.

The energy harvesting antenna 1000 electrically couples to an impedance matching network 1002 (shown in block diagram form and labeled "Z"). As the name implies, the impedance matching network 1002 matches impedance between the energy harvesting antenna 1000 and the downstream devices to ensure low reflected energy and thus efficient energy transfer to the downstream devices. The impedance matching network 1002, in turn, electrically couples to the rectifier 1004. The rectifier 1004 rectifies the alternating current energy from the energy harvesting antenna 1000, and applies the energy to either an on-chip capacitor 1006, capacitor 309 associated with the substrate 300, or both. The block diagram form showing the rectifier 1004 illustratively shows a single diode; however, the rectifier may take any suitable form, including the half-wave rectification by way of a single diode, full-wave rectification by way of a diode bridge, and rectification by switches operated as diodes (to reduce energy loss in the form of diode voltage drop). In some cases, the rectifier 1004 directly applies the rectified energy to the capacitor 1006 and/or 309 (FIG. 3), but in other cases the rectifier 1004 may further include circuitry to increase the voltage, such as a Dickson Charge Pump. In either event the rectified energy (with or without voltage step-up) is applied to the capacitor 1006 and/or 309. The voltage on the capacitor 1006 and/or 309 is referred to herein as the unregulated voltage ($V_{UNREG}$), and in some cases may be on the order of 1.6 Volts when fully charged.

The example energy harvesting circuit 302 further comprises a power management unit (PMU) 1008 defined on the substrate 300. The power management unit 1008 is electrically coupled to the capacitor 1006 and/or 309, and thus is electrically coupled to the unregulated voltage. In example systems, the power management unit 1008 comprises one or more circuits that selectively produce a regulated voltage ($V_{REG}$) from the unregulated voltage. In some cases the regulated voltage may be about 1.0 Volts. The example power management unit 1008 also produces an enable signal 1010 coupled to various other of the circuits. In accordance with example embodiments, the power management unit 1008 de-asserts the enable signal 1010 during periods of time when the energy stored on the capacitor 1006 and/or 309 is below a predetermined threshold. With the remaining circuits disabled and thus not consuming power or consuming significantly reduced power, the energy harvesting circuit 302 can more quickly charge the capacitor 1006 and/or 309 from ambient energy. Once the energy stored reaches or exceeds the predetermined threshold (again, e.g., 1.6 V), the power management unit 1008 asserts the enable signal 1010 thus enabling the remaining circuits to operate, such as sensing electrical impulses by the sensing circuit 308, applying energy to the tissue by the energy delivery circuit 306, and sending and/or receiving communications by way of the communication circuit 304.

Still referring to FIG. 10, the example energy harvesting circuit 302, in addition to or in place of harvesting ambient energy in the form of electromagnetic waves, may also be designed and constructed to harvest ambient energy in the form of electrical current flow flowing proximate to the microchip device 112. In particular, further example systems implement a set of conductive pads 1012 electrically coupled to the rectifier. The set of conductive pads 1012 may be electrically coupled to conductive pads 404 and 406 (FIG. 4) on the second side 314 of the anchoring structure 310. In other cases, the set of conductive pads 1012 may be electrically coupled to the barbed pins 800 and 802 (FIG. 8, if present), or one conductive pad of the set of conductive pads 1012 may be electrically coupled to the helical screw 900 (FIG. 9, if present). Thus, the set of conductive pads 1012 are electrically coupled to the conductive environment within the body of the patient.

In operation, the communication device 114 (FIG. 1, alone or in combination with other devices) may create charging electrical current flows through and around the heart, the charging electrical current flows having a frequency in the range of 1 Hz to 10 MHz inclusive, and in some cases between 10 kilo-Hertz (kHz) and 1 MHz inclusive. Thus, the energy harvesting circuit 302 may harvest ambient energy directed through the patient for the specific purpose of charging the microchip devices. In other cases, the conductive pads 1012 and rectifier 1004 may harvest ambient energy in the form of electrical impulses sourced by the heart itself. For example, during periods of time when the heart is beating properly, the energy harvesting circuit, by way of conductive pads 1012, may extract energy from the electrical impulses sourced by and propagating within the heart tissue. The energy may then be utilized during periods of arrhythmias to defibrillate and/or pace the heart as needed. The specification now turns to the example communication circuit 304.

FIG. 10 further shows a communication circuit 304. The communication circuit 304 is defined on the substrate 300 and is electrically coupled to the energy harvesting circuit 302, and more particularly is electrically coupled to the regulated voltage $V_{REG}$. The communication circuit comprises the processor and memory 1014 (hereafter just processor 1014), radio 1016, and a communication antenna 1018. At least a portion of the functionality of the communication circuit 304 is implemented by programs executed on the processor 1014, such as formulating messages to be sent to the communication device 114, and implementing commands received from the communication device 114. The processor 1014 is communicatively coupled to the radio 1016. Radio 1016 is communicatively coupled to the processor 1014, is coupled to the regulated voltage $V_{REG}$ to receive operational power, and likewise may be coupled to the enable signal 1010. The radio 1016 takes packet-based messages created by the processor 1014 (e.g., indications of electrical signals sensed by the sensing circuit 308) and modulates the messages for transmission. Likewise, messages received by the radio 1016 (e.g., commands to apply defibrillation and/or pacing energy) are demodulated and passed to the processor 1014, which in turn implements the commands.

To send and receive messages, the radio 1016 is electrically coupled to communication antenna 1018, illustratively shown as a diploe antenna. In example cases, the communication antenna 1018 has an operating frequency above 1 MHz, in some cases having an operating frequency of between 1 MHz and 1 Giga-Hertz (GHz) inclusive, and in specific cases between 100 MHz and 1 GHz inclusive. The communication antenna 1018 may be monolithically created on the substrate 300 by deposition of metallic material and selective etching to create metallic conductors. Other monolithically created antenna types may be equivalently used, such as bow tie antennas and patch antennas.

Still referring the FIG. 10, the communication circuit 304, in addition to or in place of communication by way of electromagnetic waves, may also be designed and constructed to communicate by inducing electrical current flow in the conductive environment of the body, such that the communication device 114 can either detect the current flow directly, or the communication device may be able to detect electric fields caused by the induced electrical current flow. In particular, further example systems implement a set of conductive pads 1020 electrically coupled to a conductive driver circuit 1022. The set of conductive pads 1020 may be electrically coupled to conductive pads 412 and 414 (FIG. 4) on the second side 314 of the anchoring structure 310. In other cases, the set of conductive pads 1020 may be electrically coupled to the barbed pins 800 and 802 (FIG. 8, if present), or one conductive pad of the set of conductive pads 1020 may be electrically coupled to the helical screw 900 (FIG. 9, if present). Thus, the set of conductive pads 1012 are electrically coupled to the conductive environment within the body of the patient. In operation, communicative electrical current flows by and between the communication device 114 and the communication circuit 304 may travel through and around the heart. The communicative electrical current flows may have a frequency in the range of 1 kHz to 1 MHz inclusive, and in some cases between 10 kHz and above to reduce interference with the electrical system of the heart. Thus, the conductive driver circuit 1022 takes packet-based messages created by the processor 1014 (e.g., indications of electrical signals sensed by the sensing circuit 308) and modulates the messages for transmission by way of electrical current flows. Likewise, messages received by the conductive driver circuit 1022 (e.g., commands to apply defibrillation and/or pacing energy) are demodulated and passed to the processor 1014, which in turn implements the commands.

FIG. 10 further shows sensing circuit 308. The sensing circuit 308 is defined on the substrate 300 and is electrically coupled to the energy harvesting circuit 302, and more particularly is electrically coupled to the regulated voltage $V_{REG}$. The sensing circuit 308 may include the processor 1014, a sensing element, a rectifier 1024, and an analog to digital (AD) converter 1026. At least a portion of the functionality of the sensing circuit 308 is implemented by programs executed on the processor 1014, such as receiving indications of the presence of electrical impulses, and/or parameters of the electrical impulses, and sending the information to the communication device 114 by way of the communication circuit 304 (in any or all the various forms). The processor 1014 is thus coupled to the AD converter 1026 and communicatively coupled to the radio 1016 and/or the conductive driver circuit 1022 in the communication circuit 304.

Sensing electrical impulses sourced by and propagating within the heart may take many forms. In one example system, the electrical impulses are sensed by way of their magnetic fields. That is, time varying electrical current flow induces magnetic fields. Inasmuch as the electrical impulses sourced by the heart are time varying, in one example system the electrical impulses are detected based on detection of associated magnetic fields. To that end, in some cases the substrate 300 may include a loop antenna 1028. The example loop antenna 1028 is shown to encircle all the other components, and is also shown to have only a single loop or turn. In other cases, the loop antenna 1028 may be disposed other than encircling the other components, and may contain multiple loops. The loop antenna 1028 may be monolithically created on the substrate 300 by deposition of metallic material and selective etching to create metallic conductors.

The example loop antenna 1028 is electrically coupled to rectifier 1024. The rectifier 1024 rectifies the electrical current induced on the loop antenna 1028, and then applies the rectified waveform to the AD converter 1026. The block diagram form showing the rectifier 1024 illustratively shows a single diode; however, the rectifier may take any suitable form, including the half-wave rectification by way of a single diode, full-wave rectification by way of a diode bridge, and rectification by switches operated as diodes. Thus, the electrical system comprising the loop antenna 1028, rectifier 1024, and AD converter 1026 may be used to detect presence of an electrical impulse, and to some extent the strength of the electrical impulse. In other cases, however, the rectifier 1024 may be omitted and the AD converter 1026 may thus digitize the waveform of the detected electrical impulse. The sensing circuit 308 may thus send an indication of the full waveform to the communication device 114 by way of the communication circuit 304, and thus the communication circuit may make defibrillation and/or pacing decisions based on the full waveform.

Still referring to FIG. 10, the sensing circuit 308, in addition to or in place of sensing the electrical impulses by way of loop antenna 1028, may also be designed and constructed to sense electrical impulses conductively. In particular, further example systems implement a set of conductive pads 1030 electrically coupled to the rectifier 1024, or if the rectifier 1024 is not implemented the conductive pads 1030 may couple to the AD converter 1026 (such as through an amplifier and/or small parallel resistance). The set of conductive pads 1030 may be electrically coupled to conductive pads 408 and 410 (FIG. 4) on the second side 314 of the anchoring structure 310. In other cases, the set of conductive pads 1030 may be electrically coupled to the barbed pins 800 and 802 (FIG. 8, if present), or one conductive pad of the set of conductive pads 1030 may be electrically coupled to the helical screw 900 (FIG. 9, if present). Thus, the set of conductive pads 1030 are electrically coupled to the conductive environment within the body of the patient. In operation, electrical impulses sourced by and propagating within the heart may be conductively sensed by the sensing circuit 308.

FIG. 10 further shows energy delivery circuit 306 defined on the substrate 300. The energy delivery circuit 306 may include the processor 1014, biphasic coupling bridge 1032, and a set of conductive pads 1034. At least a portion of the functionality of the energy delivery circuit 306 is implemented by programs executed on the processor 1014, such as receiving instructions to apply electrical energy, and sending commands to control the biphasic coupling bridge 1032. The processor 1014 is thus controllably coupled to the biphasic coupling bridge 1032. Though a single connection is shown between the processor 1014 and the biphasic coupling bridge 1032 (as a dashed line), it will be understood that multiple electrical/communicative connections may be implemented (e.g., one for each electrically controlled switch within the biphasic coupling bridge 1032).

The set of conductive pads 1034 may be electrically coupled to conductive electrodes 400 and 402 (FIG. 4) on the second side 314 of the anchoring structure 310. In other cases, the set of conductive pads 1034 may be electrically coupled to the barbed pins 800 and 802 (FIG. 8, if present), or one conductive pad of the set of conductive pads 1034 may be electrically coupled to the helical screw 900 (FIG. 9, if present). Thus, the set of conductive pads 1034 are electrically coupled to the conductive environment within the body of the patient. In operation, electrical energy applied to the heart tissue to defibrillate and/or pace the heart tissue is applied by way of the set of conductive pads 1034.

Biphasic coupling bridge 1030 couples between a source of electrical energy and the set of conductive pads 1034. In some cases, the source of electrical energy for defibrillation and/or pacing is derived from regulated voltage $V_{REG}$ (as shown by the bubble "A'" (A prime) coupled to the biphasic coupling bridge 1032). In other cases, perhaps where higher voltage and/or current is needed, the source of electrical energy for defibrillation and/or pacing is derived from unregulated voltage $V_{UNREG}$ (as shown by the bubble "A" coupled to the biphasic coupling bridge 1032). The example biphasic coupling bridge 1032 comprises four electrically controlled switches 1036, 1038, 1040, and 1042. Although shown as contact switches so as not to unduly clutter the figure, in practice the switches may be any electrically controlled switch device, such as field effect transistors (FETs). The source of electrical energy (e.g., either the regulated voltage $V_{REG}$ or the unregulated voltage $V_{UNREG}$) couples to an upper rail of the biphasic coupling bridge 1032, while the lower rail of the biphasic coupling bridge 1032 is connected to common or ground defined on the substrate 300. A first conductive pad of the set of conductive pads 1034 is coupled between electrically controlled switches in a first leg of the bridge (e.g., between electrically controlled switches 1036 and 1040), and a second conductive pad of the set of conductive pads 1034 is couple between electrically controlled switches in a second leg of the bridge (e.g., between electrically controlled switches 1038 and 1042).

Thus, by selective control of the electrically controlled switches 1036, 1038, 1040, and 1042, the energy delivery circuit 306 can apply electrical energy biphasically (i.e., with alternating polarities) if desired. Consider, as an example, that the energy delivery circuit 306 has received a command from the communication circuit to apply biphasic electrical energy for purposes of defibrillation and/or pacing. Initially, the biphasic coupling bridge may make electrically controlled switches 1036 and 1042 conductive, and make electrically controlled switches 1038 and 1040 non-conductive, thus applying the electrical energy across the conductive pads 1034 with a first polarity. After a predetermined amount of time, the processor 1014 may make electrically controlled switches 1036 and 1042 non-conductive, and make electrically controlled switches 1038 and 1040 conductive, thus applying the electrical energy across the conductive pads 1034 with a second polarity, opposite the first polarity. After a predetermined amount of time, the processor 1014 may make all the electrically controlled switches 1036 and 1042 non-conductive, thus ending the application of electrical energy to the heart tissue. In yet still other cases, the processor 1014 may command the biphasic coupling bridge to couple the electrical energy in only one, perhaps predetermined, polarity.

As a non-limiting example, the electrical current applied as part of the defibrillation and/or pacing can be positive or negative. The pulse width of the current may be varied from one microsecond to one second, and the amplitude of the electrical current may be varied from one micro-Amp to one Amp (e.g., by operating the electrically controlled switches 1036-1042 in the form of transistors within their active regions to control voltage drop across the transistors).

Figure 11:
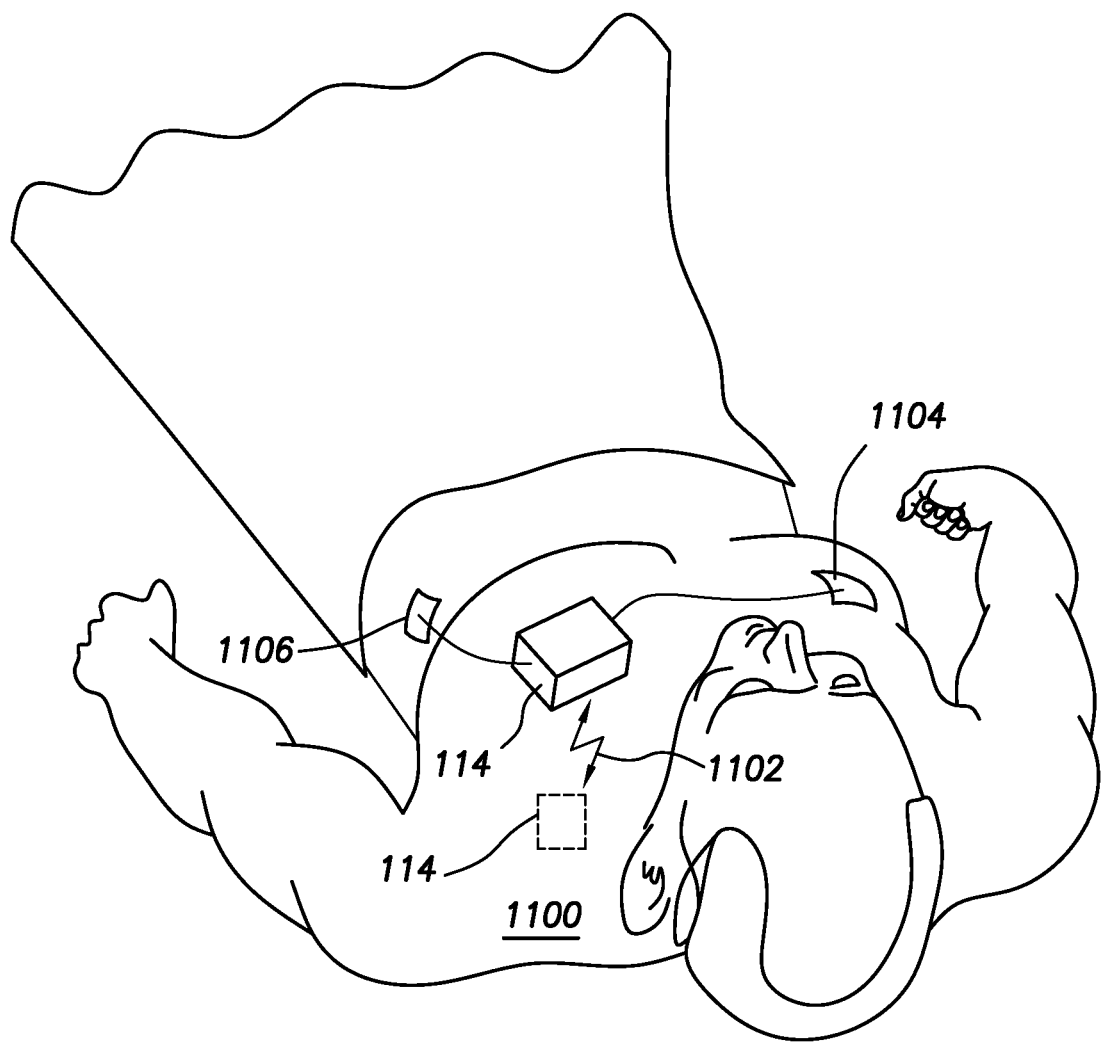
FIG. 11 shows a perspective view of a patient and an example communication device in accordance with at least some embodiments.

FIG. 11 shows a perspective view of a patient and an example communication device 114 in accordance with at least some embodiments. In particular, shown in FIG. 11 is a patient 1100 along with several examples of a communication device 114. In some cases, the communication device may be implanted subcutaneously (e.g., under the skin but outside the rib cage), as shown by communication device 114 shown in dashed lines. In other cases, the communication device 114 may reside fully outside the body, such as illustrated by communication device 114 shown in solid lines. In yet still other cases, the functionality of the communication device 114 may be split between a portion placed subcutaneously, and an external portion (i.e., both communication devices 114 shown in FIG. 11). In such cases, the external portion and internal portion may communicate wirelessly, as shown by arrow 1102.

FIG. 11 further shows an example of communicating with the microchip devices coupled to the heart (none visible in FIG. 11) and/or powering the microchip devices conductively. That is, FIG. 11 shows a first electrical contact 1104 coupled to the chest of the patient 1100, and electrically coupled to the external version of the communication device 114. A second electrical contact 1106 is coupled to the rib cage of the patient 1100 below the chest, thus forming a conduction path proximate to the patient's heart. By applying electrical energy across the electrical contacts (at the frequencies discussed above), the communication device 114 may power microchip devices coupled to the patient's heart. Likewise, by detecting minute voltages across the electrical contacts, the electrical fields caused by communicative electrical signals inducing current within the tissue of the patient, the microchip devices may communicate with the communication device 114. While FIG. 11 shows the electrical contacts 1104 and 1106, and corresponding electrical leads, external to the patient's body, in the case of the subcutaneously placed communication device 114 the leads and electrical contacts too could be subcutaneously placed. Finally, whether the communication device 114 is external, or internal, or combinations thereof, the communication device 114 may still direct electromagnetic waves to the heart to provide ambient energy for energy harvesting and/to communicate with the microchip devices.

Figure 12:
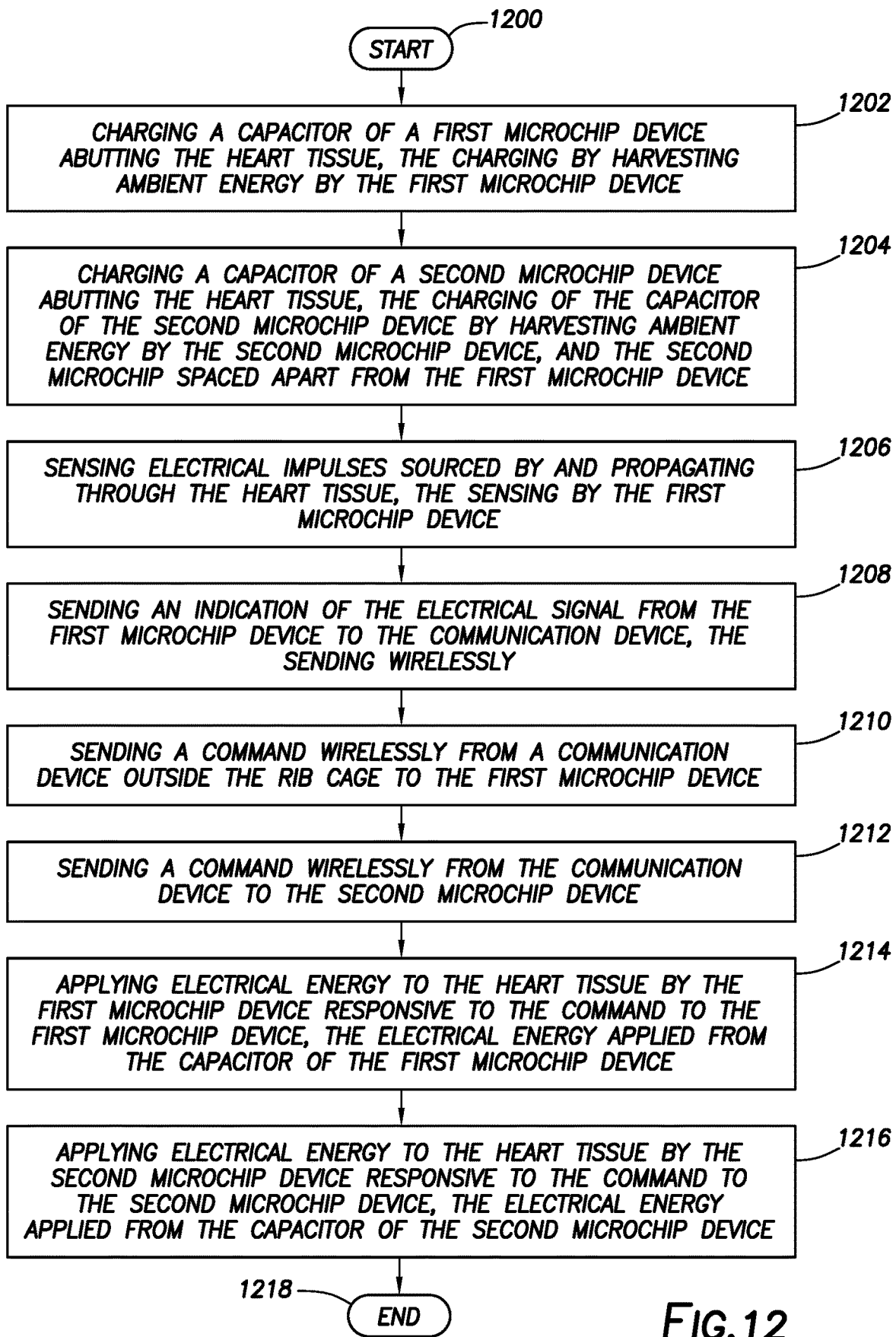
FIG. 12 shows a method in accordance with at least some embodiments.

FIG. 12 shows a method in accordance with at least some embodiments. In particular, the method starts (block 1200) and comprises: charging a capacitor of a first microchip device abutting the heart tissue, the charging by harvesting ambient energy by the first microchip device (block 1202); charging a capacitor of a second microchip device abutting the heart tissue, the charging of the capacitor of the second microchip device by harvesting ambient energy by the second microchip device, and the second microchip spaced apart from the first microchip device (block 1204); sensing electrical impulses sourced by and propagating through the heart tissue, the sensing by the first microchip device (block 1206); sending an indication of the electrical signal from the first microchip device to the communication device, the sending wirelessly (block 1208); sending a command wirelessly from a communication device outside the rib cage to the first microchip device (block 1210); sending a command wirelessly from the communication device to the second microchip device (block 1212); applying electrical energy to the heart tissue by the first microchip device responsive to the command to the first microchip device, the electrical energy applied from the capacitor of the first microchip device (block 1214); and applying electrical energy to the heart tissue by the second microchip device responsive to the command to the second microchip device, the electrical energy applied from the capacitor of the second microchip device (block 1216). Thereafter the method ends (block 1218), likely to be restarted on the next heart beat.

The above discussion regarding energy harvesting related to electric fields applied to a sample volume is meant to be illustrative of the principles and various embodiments. Numerous variations and modifications will become apparent to those skilled in the art once the above disclosure is fully appreciated. It is intended that the following claims be interpreted to embrace all such variations and modifications.

We claim:

1. An implantable cardiac device, comprising:
one or more treatment devices implantable within, on, and/or proximate a heart, at least one treatment device comprising:
an energy harvesting circuit configured to harvest ambient energy, including ambient electrical, magnetic, and/or electromagnetic energy;
an energy delivery circuit coupled to a set of electrodes; and
a communication circuit configured to control the energy delivery circuit to deliver energy via one or more electrodes from the set of electrodes in response to wireless control signals
wherein the one or more treatment devices includes an array of microchip devices, including one or more microchip devices comprising a semiconductor substrate including:
the communication circuit;
the energy harvesting circuit; and
the energy delivery circuit.

2. The device of claim 1, wherein at least one of the one or more treatment devices is adapted to deliver energy via at least one of the one or more electrodes below about 1.0 Joule.

3. The device of claim 1, further comprising:
a communication device configured to communicate the wireless control signals to the communication circuit of at least one of the one or more treatment devices,
wherein the wireless control signals include information used to selectively drive the one or more electrodes to deliver energy to heart tissue.

4. The device of claim 3, wherein the communication device is configured to substantially simultaneously drive a plurality of electrodes from the one or more electrodes.

5. The device of claim 3, wherein the communication device is configured to sequentially drive a plurality of electrodes from the one or more electrodes.

6. The device of claim 5, wherein the communication device is configured to drive the plurality of electrodes to apply electrical energy to the heart tissue sequentially along a predefined path.

7. The device of claim 3, wherein the communication device is configured to drive a plurality of electrodes from the one or more electrodes to substantially simultaneously apply electrical energy.

8. The device of claim 3, wherein the communication device is configured to drive the one or more electrodes to pace and/or defibrillate the heart.

9. The device of claim 8, wherein the one or more electrodes includes electrodes configured for placement in the Vein of Marshall.

10. The device of claim 9, wherein at least one treatment device is configured for placement at or near the entrance to the Vein of Marshall to at least partially control the electrodes in the Vein of Marshall.

11. The device of claim 9, wherein at least one treatment device is configured for placement within the Vein of Marshall to at least partially control the electrodes in the Vein of Marshall.

12. The device of claim 8, wherein the one or more electrodes includes electrodes configured for placement in one or more branches of the Coronary Sinus.

13. The device of claim 12, wherein at least one treatment device is configured for placement at or near the entrance to the Coronary Sinus to at least partially control the electrodes in the one or more branches of the Coronary Sinus.

14. The device of claim 3, wherein the communication device comprises an antenna configured to transmit electromagnetic waves to communicate with the one or more treatment devices and/or electrodes from the set of electrodes.

15. The device of claim 3, wherein the communication device comprises an antenna configured to transmit electromagnetic waves to provide at least a portion of the ambient energy to at least one of the one or more treatment devices.

16. The device of claim 1, wherein the one or more microchip devices further include:
a sensing circuit configured to sense electrical impulses propagating within or on the outside of the heart.

17. The device of claim 1, wherein at least one microchip device from the array of microchip devices is individually addressable and controllable.

18. The device of claim 1, wherein at least one microchip device from the array of microchip devices is configured for endocardial placement, epicardial placement, venous system placement, and/or arterial system placement.

19. The device of claim 1, wherein:
the energy harvesting circuit includes at least one capacitor configured to store at least a portion of the ambient energy.

20. The device of claim 19, wherein the energy harvesting circuit further comprises:
at least one energy harvesting antenna and/or conducive pads;
a rectifier configured to rectify alternating current (AC) voltage from the at least one energy harvesting antenna and/or conductive pads and to store rectified energy in the at least one capacitor; and
a power management unit configured to produce a regulated DC voltage from the rectified energy stored in the at least one capacitor.

21. A method of cardiac treatment, comprising:
implanting one or more treatment devices within, on, and/or proximate a heart, at least one treatment device comprising:
an energy harvesting circuit;
an energy delivery circuit coupled to a set of electrodes; and
a communication circuit,
wherein the one or more treatment devices includes an array of microchip devices, including one or more microchip devices comprising a semiconductor substrate including:
the communication circuit;
the energy harvesting circuit; and
the energy delivery circuit;
harvesting ambient energy, including ambient electrical, magnetic, and/or electromagnetic energy, with the energy harvesting circuit; and
delivering energy via one or more electrodes from the set of electrodes in response to wireless control signals received by the communication circuit.

22. The method of claim 21, wherein the delivering energy includes delivering energy below about 1.0 Joule by at least one of the one or more electrodes.

23. The method of claim 21, further comprising:
a communication device communicating the wireless control signals to the communication circuit of at least one of the one or more treatment devices,
wherein the wireless control signals include information used to selectively drive the one or more electrodes to deliver energy to heart tissue.

24. The method of claim 23, wherein the delivering energy includes substantially simultaneously driving a plurality of electrodes from the one or more electrodes.

25. The method of claim 23, wherein the delivering energy includes sequentially driving a plurality of electrodes from the one or more electrodes.

26. The method of claim 25, wherein the delivering energy includes driving the plurality of electrodes to apply electrical energy to the heart tissue sequentially along a predefined path.

27. The method of claim 23, wherein the delivering energy includes driving a plurality of electrodes from the one or more electrodes substantially simultaneously.

28. The method of claim 23, wherein the delivering energy includes driving the one or more electrodes to pace and/or defibrillate the heart.

29. The method of claim 28, further comprising placing electrodes from the one or more electrodes in the Vein of Marshall and pacing and/or defibrillating the heart using the electrodes in the Vein of Marshall.

30. The method of claim 29, further comprising placing at least one treatment device at or near the entrance to the Vein of Marshall and at least partially controlling the electrodes in the Vein of Marshall using the at least one treatment device.

31. The method of claim 29, further comprising placing at least one treatment device within the Vein of Marshall to at least partially control the electrodes in the Vein of Marshall.

32. The method of claim 28, further comprising placing electrodes from the one or more electrodes in one or more branches of the Coronary Sinus and pacing and/or defibrillating the heart using the electrodes in the one or more branches of the Coronary Sinus.

33. The method of claim 32, further comprising placing at least one treatment device at or near the entrance to the Coronary Sinus and at least partially controlling the electrodes in the one or more branches of the Coronary Sinus using the at least one treatment device.

34. The method of claim 23, wherein the communication device comprises an antenna and the method includes the antenna transmitting electromagnetic waves to communicate with the one or more treatment devices and/or electrodes from the set of electrodes.

35. The method of claim 23, wherein the communication device comprises an antenna and the method includes the antenna transmitting electromagnetic waves to provide at least a portion of the ambient energy to at least one of the one or more treatment devices.

36. The method of claim 21, wherein the one or more microchip devices further include a sensing circuit and the method includes the sensing circuit sensing electrical impulses propagating within or on the outside of the heart.

37. The method of claim 23, further comprising the communication device individually addressing and controlling at least one microchip device from the array of microchip devices.

38. The method of claim 21, further comprising placing at least one microchip device from the array of microchip devices in the endocardium, epicardium, venous system, and/or arterial system.

39. The method of claim 21, wherein the energy harvesting circuit includes at least one capacitor, and the method includes the energy harvesting circuit storing at least a portion of the ambient energy in the at least one capacitor.

40. The method of claim 39, wherein the energy harvesting circuit further comprises:
at least one energy harvesting antenna and/or conducive pads,
a rectifier, and
a power management unit coupled to the at least one capacitor, and
the method includes:
the rectifier rectifying alternating current (AC) energy from the at least one energy harvesting antenna and/or conductive pads and storing a rectified energy in the at least one capacitor; and
the power management unit producing a regulated DC voltage from the rectified energy stored in the at least one capacitor.

* * * * *